US012653523B2

(12) United States Patent
Walish et al.

(10) Patent No.: US 12,653,523 B2
(45) Date of Patent: Jun. 16, 2026

(54) ENDOSCOPIC SUTURING DEVICE WITH NEEDLE LOADER

(71) Applicant: EnVision Endoscopy, Inc., Somerville, MA (US)

(72) Inventors: Judy Walish, Boston, MA (US); Azadeh Khanicheh, Somerville, MA (US)

(73) Assignee: EnVision Endoscopy, Inc., Somerville, MA (US)

( * ) Notice: Subject to any disclaimer, the term of this patent is extended or adjusted under 35 U.S.C. 154(b) by 721 days.

(21) Appl. No.: 17/832,453

(22) Filed: Jun. 3, 2022

(65) Prior Publication Data

US 2022/0387017 A1 Dec. 8, 2022

Related U.S. Application Data

(60) Provisional application No. 63/196,410, filed on Jun. 3, 2021.

(51) Int. Cl.
| | |
|---|---|
| *A61B 17/04* | (2006.01) |
| *A61B 34/00* | (2016.01) |
| *A61B 17/00* | (2006.01) |

(52) U.S. Cl.
CPC .......... *A61B 17/0469* (2013.01); *A61B 34/71* (2016.02); *A61B 2017/00296* (2013.01); *A61B 2017/0053* (2013.01)

(58) Field of Classification Search
CPC .... A61B 2017/06028; A61B 17/06114; A61B 17/0482; A61B 17/0491; A61B 17/0625; A61B 17/0469; A61B 17/062
See application file for complete search history.

(56) References Cited

U.S. PATENT DOCUMENTS

| | | | |
|---|---|---|---|
| 7,976,555 B2 | 7/2011 | Meade et al. | |
| 7,993,354 B1 | 8/2011 | Brecher et al. | |
| 9,370,354 B1 | 6/2016 | Martin et al. | |
| 2006/0161185 A1* | 7/2006 | Saadat ............... | A61B 17/0487 606/153 |
| 2009/0024145 A1* | 1/2009 | Meade ............... | A61B 17/0491 606/144 |

(Continued)

OTHER PUBLICATIONS

International Search Report and Written Opinion for International Application No. PCT/US2022/032245 mailed Oct. 17, 2022, 15 pages.

(Continued)

*Primary Examiner* — Katherine H Schwiker
(74) *Attorney, Agent, or Firm* — Nutter McClennen & Fish LLP

(57) ABSTRACT

A system loads an endoscopic needle into an endoscopic suturing device. The system includes a loading tool having a handle portion configured to be manipulated by a medical professional. The system also includes a needle cover coupling portion configured to removably couple with a needle cover. The needle cover is configured to couple with a delivery housing. The needle cover is further configured to secure a needle within a needle track of the delivery housing when coupled with the delivery housing. The loading tool is configured to couple the needle cover with the delivery housing. The loading tool is further configured to uncouple the needle cover from the delivery housing.

21 Claims, 30 Drawing Sheets

(56) References Cited

U.S. PATENT DOCUMENTS

2010/0016866 A1\* 1/2010 Meade ............. A61B 17/06114
606/139
2015/0127024 A1 5/2015 Berry

OTHER PUBLICATIONS

Extended European Search Report for European Patent Application
No. 22816966.0 dated Jun. 12, 2025, 14 pages.

\* cited by examiner

ENDOSCOPIC SUTURING DEVICE WITH NEEDLE LOADER

PRIORITY

This patent application claims the benefit of U.S. Provisional Patent Application No. 63/196,410, entitled ENDOSCOPIC SUTURING DEVICE WITH NEEDLE LOADER filed Jun. 3, 2021, which is hereby incorporated by reference in its entirety.

FIELD OF THE INVENTION

Illustrative embodiments of the invention generally relate to endoscopic devices and, more particularly, the various embodiments relate to a replaceable needle and suture loading assembly for endoscopic devices.

BACKGROUND

Full-thickness gastrointestinal defects such as perforation, anastomotic leak, and fistula are severe conditions caused by various types of pathologies. Such conditions are more likely to require intensive care, involve long hospital stays, and have high rates of morbidity and mortality. Due to their minimally invasive nature, endoscopic suturing techniques are desirable for the closure of such conditions. While such techniques are desirable, loading and changing needles and sutures, such as for changing suture size during a medical procedure, may be difficult and expensive. Therefore, a need exists for an inexpensive and easy system for loading and replacing a needle and suture for endoscopic procedures.

SUMMARY

In accordance with one embodiment, a system loads an endoscopic needle into an endoscopic suturing device. The system includes a loading tool having a handle portion configured to be manipulated by a medical professional. The system also includes a needle cover coupling portion configured to removably couple with a needle cover. The needle cover is configured to couple with a delivery housing. The needle cover is further configured to secure a needle within a needle track of the delivery housing when coupled with the delivery housing. The loading tool is configured to couple the needle cover with the delivery housing. The loading tool is further configured to uncouple the needle cover from the delivery housing.

In various embodiments, the loading tool is configured to secure the needle cover to the delivery housing. Additionally, or alternatively, the loading tool may be configured to unsecure the needle cover from the delivery housing. Among other things, the loading tool may include a needle holding portion. The needle holding portion may hold a needle. The needle may be coupled with a suture at the suture end of the needle. In some embodiments, the system includes an endoscopic suturing device comprising a delivery housing. Furthermore, the system may include a drive mechanism configured to control movement of the needle. The drive mechanism may include a cable and a pawl.

In some embodiments, the delivery housing includes one or more slots configured to receive one or more tabs of the needle cover. The slots may include a protrusion configured to interfere with the one or more tabs of the needle cover. The delivery housing may have an opening to receive one or more tabs into the one or more slots. The needle cover may secure to the delivery housing by a user pressing down the loading tool and/or rotating the loading tool in a first direction. The needle cover may be configured to unsecure from the delivery housing by a user pulling up the loading tool and/or rotating the loading tool in a second direction opposite the first direction.

In accordance with another embodiment, a method loads an endoscopic needle into an endoscopic suturing device. The method provides a loading system having a loading tool with a handle portion configured to be manipulated by a medical professional. The tool includes a needle cover coupling portion configured to removably couple with a needle cover. The system further includes a needle cover configured to couple with a delivery housing. The needle cover is configured to secure a needle within a needle track of the delivery housing when coupled with the delivery housing. The system also has a needle coupled to the loading tool and/or the needle cover. The method positions the needle within a needle track of a delivery housing of an endoscopic suturing system. The needle cover is secured to the delivery housing by using the loading tool. The loading tool is then uncoupled from the needle cover and/or the needle.

In some embodiments, securing the needle cover to the delivery housing includes rotating the loading tool in a first direction. Uncoupling the loading tool from the needle cover and/or the needle includes a user pulling up on the loading tool with respect to the needle cover and/or the needle. Furthermore, in some embodiments coupling the loading tool with the needle cover and/or the needle includes pressing down the loading tool onto the needle cover and/or the needle. Unsecuring the needle cover from the delivery housing includes rotating the loading tool.

In some embodiments, the method couples the loading tool with the needle cover and/or the needle. The needle cover may be unsecured from the delivery housing by using the loading tool. Coupling the loading tool with the needle provides a tactile feel to the medical professional. Additionally, the method may couple the needle with a drive mechanism. The drive mechanism may control the needle to suture a patient.

In accordance with another embodiment, a method couples an arcuate needle and a needle cover onto an endoscopic attachment. The method receives the arcuate needle within the needle cover that is coupled to a needle loader. A first fastener within the needle loader is coupled with a second fastener within the endoscopic attachment by relative compression, rotation, or both. The method decouples the first fastener and the second fastener by relative tension, rotation, or both. Decoupling the first fastener and the second fastener disconnects the needle loader from the needle cover while the needle cover and the arcuate needle are coupled to the endoscopic attachment.

The first fastener, the second fastener, or both may include a snap, a tab, a flexure, a pin, a groove, a slot, or any combination thereof.

In accordance with yet another embodiment, an endoscopic suture exchange kit includes a needle loader, an arcuate needle with a suture, and an endoscopic suturing needle cover that is coupled to the needle loader. The cover is configured to be rotatably couplable to the suturing device delivery housing.

In accordance with yet another embodiment, a method to exchange needle/suture includes aligning a suture exchange system with a suture device by an alignment indicator. The method locks a needle cover and a needle into a delivery housing with rotational movement, a linear movement, or both. The needle loader is uncoupled from needle cover and the needle.

The method may then remove the needle loader. The method may also align the needle loader to the suture device. The needle loader may be coupled with needle and needle cover. The needle cover may be unlocked with a rotational movement, a linear movement, or both. The suture exchange system may be removed from the suture device.

BRIEF DESCRIPTION OF THE DRAWINGS

Those skilled in the art should more fully appreciate advantages of various embodiments of the invention from the following "Detailed Description", discussed with reference to the drawings summarized immediately below.

DETAILED DESCRIPTION

Figure 1:
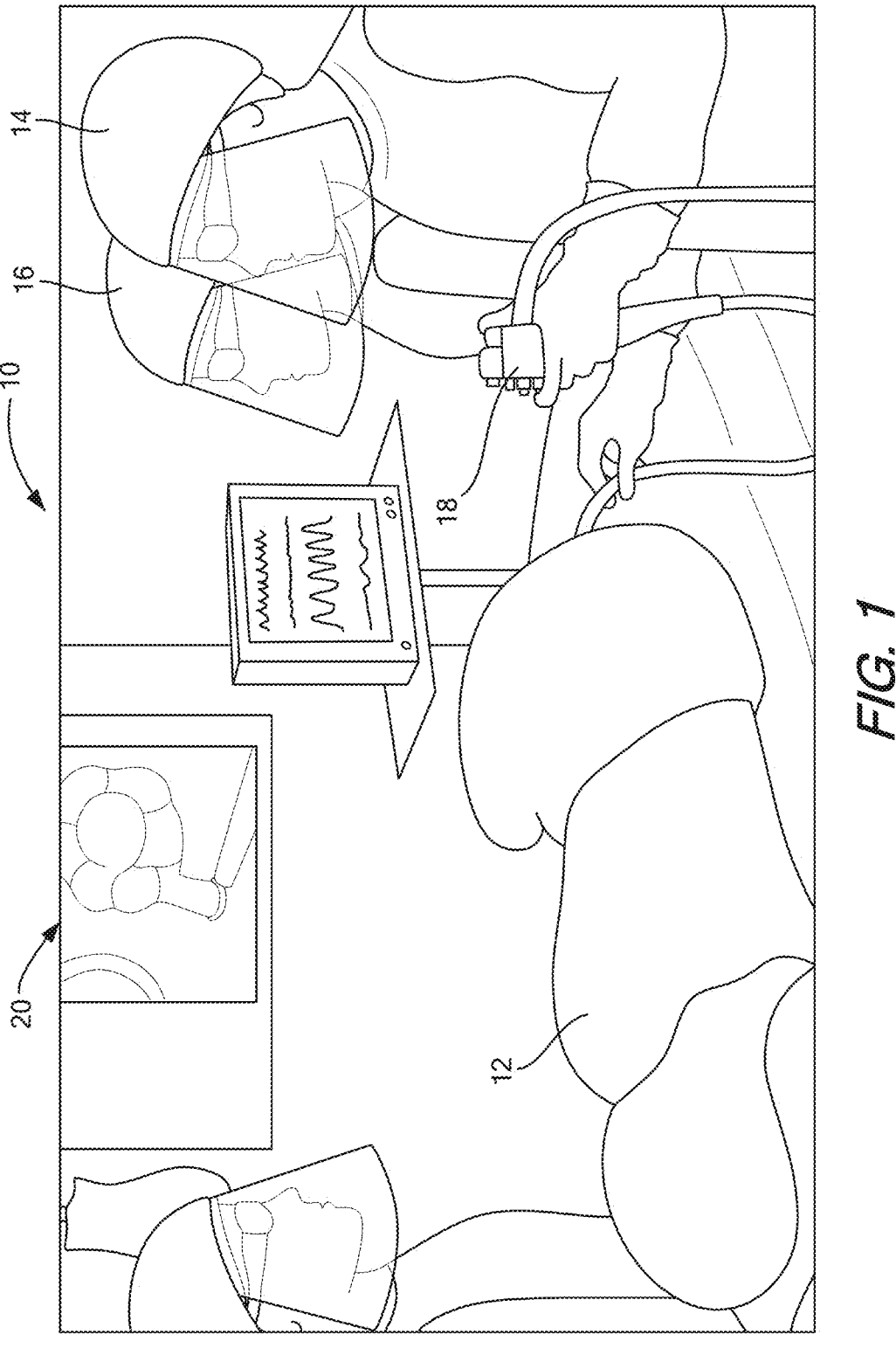
FIG. 1 depicts a patient undergoing a medical procedure in a hospital environment in accordance with illustrative embodiments of the invention.

In illustrative embodiments a needle loading system is used to load an arcuate needle onto an end of an endoscopic suturing device. The needle loading system includes an arcuate needle coupled with a suture, a needle cover, and a loading tool (also referred to as a load device). The loading tool is used to couple the needle and the needle cover with the endoscopic suturing device. The loading tool is then removed, and the needle may be used for a suturing procedure. After the needle has been used to suture, the loading tool may also be used to unload the needle and the needle cover from the endoscopic suturing device. Details of illustrative embodiments are provided below. Illustrative embodiments provide a method and apparatus enables easy and inexpensive loading, removal, and replacement of needles and sutures on an endoscopic suturing system.

In various embodiments, the needle, needle cover, and loading tool are provided in an unassembled configuration. In an assembled primed configuration, the needle cover covers the arcuate needle and suture, and the loading tool engages the needle cover and/or the needle. The term primed refers to whether the suture is available to be used for the suturing procedure by the medical professional. For example, a new loading system with a new suture includes a primed needle that is ready for suturing. However, a used or spent suture is in an unprimed configuration. However, it should be understood that the unprimed configuration may include some portion of the original suture, as the medical professional may cut the suture along some length, leaving some portion of the suture coupled to the needle in the unprimed configuration. Both the primed and unprimed assembled configurations may be generally referred to as a coupled configuration.

Preferably, illustrative embodiments provide the loading system as a kit in an assembled configuration. A cuff attaches to the distal end of an endoscope with an attached housing for receiving the arcuate needle. The needle loading system engages with the delivery housing in an initial unsecured primed configuration. The needle loading system is secured to the delivery housing, thereby defining a secured primed configuration. The loading tool is then uncoupled from the needle cover and needle (e.g., by pulling the tool away relative to the needle cover), leaving the needle cover with the needle coupled with the delivery housing. At this point, the suturing system is in a delivery configuration, ready to be positioned within the patient for suturing. The delivery housing has control wires for controlling the suturing during a medical procedure. After the patient has been sutured or if a new suture is required, the suturing system is removed from the patient. The cut suture is left inside the patient (e.g., the medical practitioner cuts the suture endoscopically). The loading tool is again coupled with the needle and/or the needle cover, at which point the system is in the secured unprimed configuration. The loading tool is used to remove the needle cover and/or the needle (e.g., by rotating the tool in the opposite direction to the securing direction) to achieve the unsecured unprimed configuration. The entire needle loading system may then be lifted off of the housing, at which point the loading system is in the assembled unprimed configuration. The needle loading system may be disposed of. If a new needle and suture is necessary, the process may be repeated with a new loading system.

FIG. 1 schematically shows a patient 12 lying on a surgical table or examination table in a hospital environment 10 in accordance with illustrative embodiments of the invention. The environment 10 may be, for example, within an endoscopy unit of the hospital. The endoscopy unit may include medical professionals 14 (e.g., gastroenterologists or surgeons), trained nurses 16, and a variety of medical devices. For example, the medical devices may include an endoscope 18, a video display 20, and other equipment. Procedures performed within the endoscopy unit may include gastrointestinal endoscopy (such as gastroscopy, colonoscopy, ERCP, and endoscopic ultrasound), bronchoscopy, cystoscopy, or other more specialized procedures.

Figure 2A:
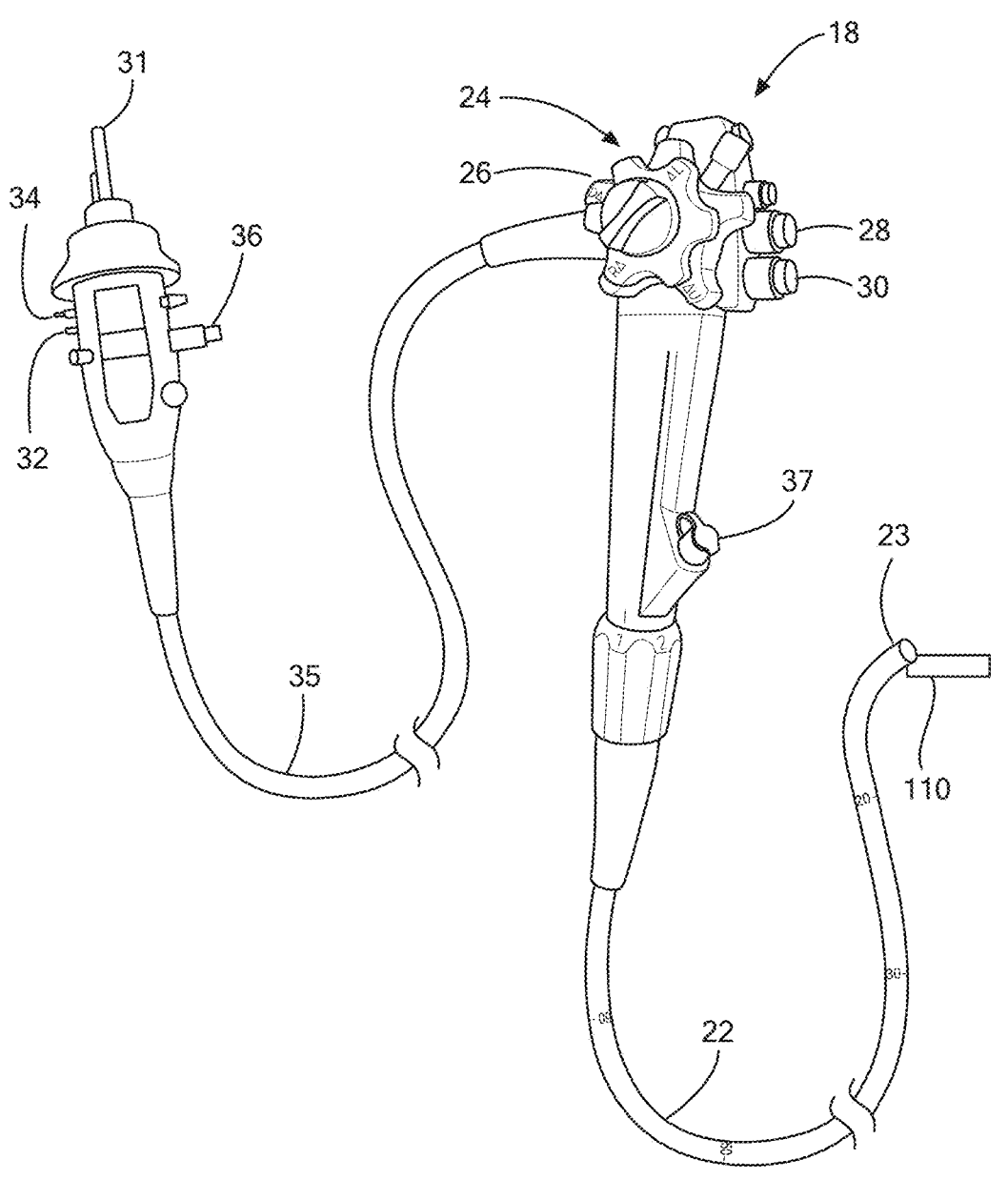
FIG. 2A depicts an endoscope in accordance with illustrative embodiments of the invention.
Figure 2B:
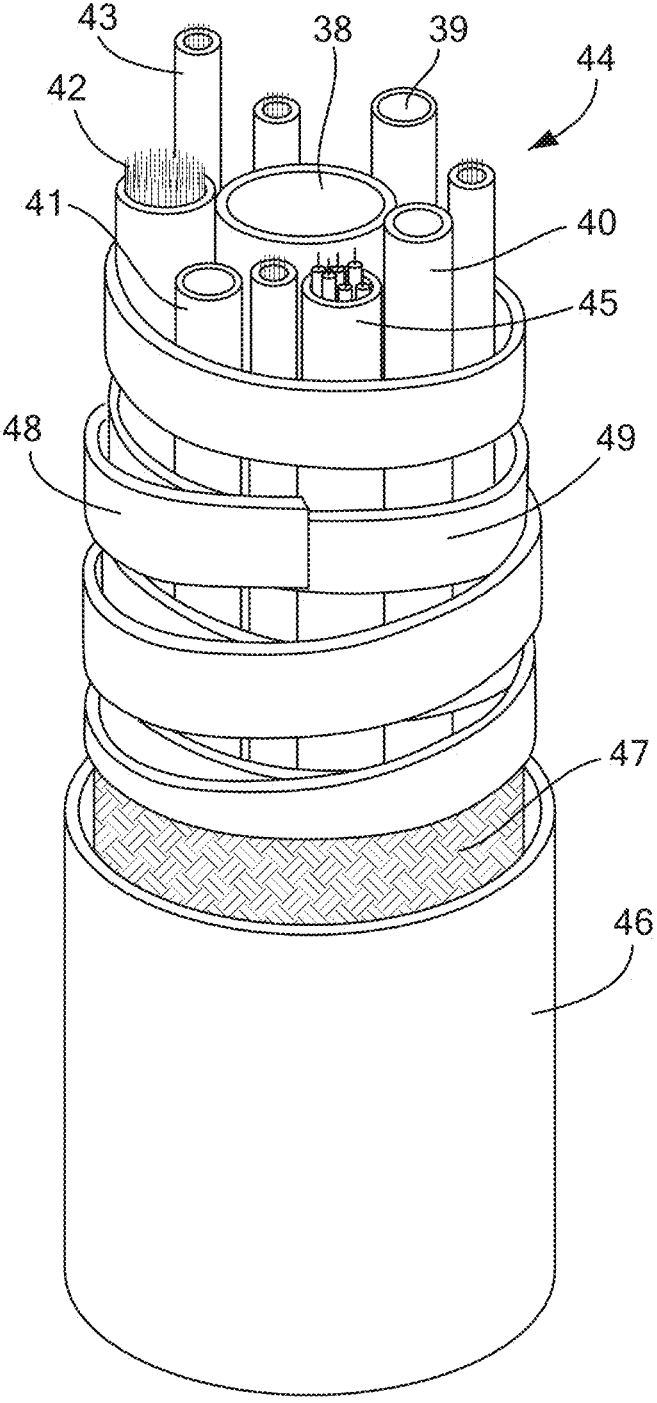
FIG. 2B depicts a partially exposed view of the insertion tube in accordance with illustrative embodiments of the invention.

FIGS. 2A-2B schematically show an endoscope 18 in accordance with illustrative embodiments of the invention. As known by those in the art, flexible endoscopes 18 (e.g., colonoscope, gastroscope) are positioned into the body of the patient 12 through the body's natural orifices (e.g., mouth, anus). To that end, the endoscope 18 has a long and flexible insertion tube 22 that is adjustable to the natural pathways within the body. Furthermore, the endoscope 18 has a number of channels running through the insertion tube 22. One of these channels is a working channel, through which tools may be advanced to a distal end 23 of the insertion tube 22.

The endoscope 18 may be contrasted with other devices such as laparoscopes, which are not inserted into the patient's 12 natural orifices. Instead, laparoscopes are inserted into one of the access holes made in the patient 12 during a laparoscopic procedure. Usually, three access holes are made for laparoscopy procedures, one for the rigid scope, and two ports for the tools such as forceps, scissor, suture, etc. Laparoscopes have a non-flexible, rigid, and short insertion tube that is sent through one of the access holes into the body. Generally, laparoscopes do not have a working channel for running tools therethrough. In contrast, the insertion tube 22 of the endoscope 18 (colonoscope, gastroscope) is flexible to travel through the body's natural orifices and has a working channel. Various embodiments may be used with a variety of scopes, such as laparoscopes. However, preferred embodiments are used with a flexible insertion tube 22.

The endoscope 18 has a control section 26 to help guide the insertion tube 22 through the patient's 12 bodily pathways (e.g., the winding GI tract). To that end, the endoscope 18 includes control dials 26 that allow control of the position and orientation of the insertion tube 22 (e.g., bending of the distal end 23 up or down, and right or left). Like many endoscopes, the endoscope 18 may have a plurality of imaging controls, such as an image freeze button and image capture button. There may also be control chromoendoscopy buttons that may change the color of the video in the display 20. The control section 24 may also include a suction button 28 and an air/water button 30. The endoscope 18 may be connected to a light supply via a light guide 31, an air supply via an air supply connector 32, a water supply via a water supply connector 34, and a suction supply via a suction connector 36. Thus, light, air, water, and/or suction, may be delivered through the umbilical cord 35 to the distal end 23 of the insertion tube 22 through the various aforementioned channels.

Water, air, suction, and other functions may selectively be applied at the distal end 23 via separate channels within the insertion tube 22. For example, the user may press the water button 30 to selectively spray water out of the distal end 23. To that end, water is pulled from an external water supply through the water supply connector 34, passes through an umbilical cord 35 of the endoscope 18, and then goes down the insertion tube 22 and out of the distal end 23. A similar process is followed for other functions, including light and suction. Each of these functions may have a dedicated channel within the endoscope 18.

In various embodiments, a cuff 110 is coupled to the distal end 23. The cuff 110 connects a delivery housing 109, as discussed below, to the distal end of the endoscope 18. By utilizing a cuff, the delivery housing 109 may easily be removed and replaced on the endoscope 18. The cuff 110 may fit on the exterior of the endoscope 18 or on the interior of the endoscope 18.

FIG. 2B schematically shows a partially exposed view of the insertion tube 22 in accordance with illustrative embodiments. The insertion tube 22 has a plurality of channels 38-41 and wires 42-45 within the insertion tube 22 that are configured to provide various utility to the endoscope 18. For example, the insertion tube 22 includes the working channel 38, an air channel 39, a water channel 40, and a water jet channel 41. The insertion tube 22 may also include light guide fibers 42, a wire for adjustable stiffness 43, angulation wires 44, and CCD signal wires 45, among other things. These channels 38-41 and wires 42-45 are within a housing of the insertion tube 22. The housing of the insertion tube 22 may include an out outer polymer top coat and base layer 46. Underneath the polymer top coat 46 may be a stainless steel wire mesh 47, along with an outer spiral metal band 48 an inner spiral metal bands 49.

Figure 3A:
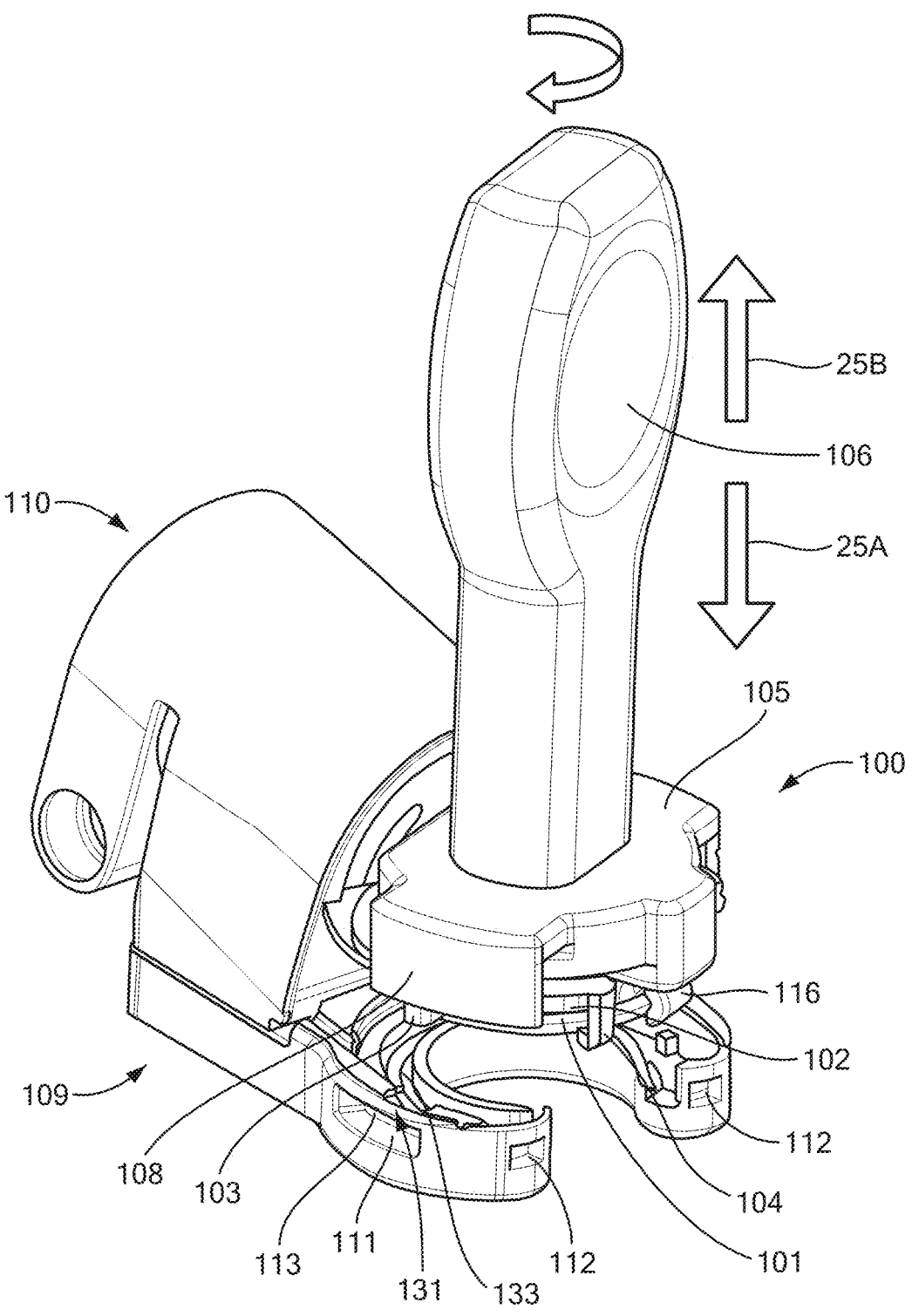
FIG. 3A depicts the needle loading system as it is about to be engaged with the delivery housing and endoscope cap in accordance with illustrative embodiments of the invention.

FIG. 3A schematically shows a needle loading system 100 in accordance with illustrative embodiments. The needle loading system 100 may be configured to couple with a needle suturing device, for example with a portion of the cuff 110 coupled to the distal end 23 of the endoscope 18. The cuff 110 may include a delivery housing 109. However, in some embodiments, the delivery housing 109 may be integrated into the endoscope 18 itself. The needle loading system 100 therefore may be configured to couple with the endoscope 18 directly, or to any other part of the suturing device. However, in preferred embodiments, the needle 101 is positioned into the delivery housing 109 such that the needle 101 is operatively coupled with a control system for the suturing device, which allows the medical professional 14 to control suturing.

In various embodiments, the needle loading system 100 includes an arcuate needle 101, a needle cover 102, and a loading tool 105. The arcuate needle 101 is used by the medical professional 14 for a suturing procedure when the needle 101 is coupled with the suturing device. The needle cover 102 helps retain the needle 101 in an appropriate position relative to the suturing device. The loading tool 105 delivers the needle 101 and the needle cover 102 to the suturing device. The loading tool 105 is then manipulated to secure the needle cover 102 to the suturing device. The loading tool 105 is then removed, and the suturing procedure is performed. After the suturing procedure is completed, or if a new suture is needed, the loading tool is recoupled with the needle cover 102 and manipulated to unsecure the needle cover 102 from the suturing device. The tool 105, cover 102 and needle 101 may be removed from the suturing device. If another suture is needed, the process may be repeated by using a second needle loading system 100 as described above. The process may be repeated as many times as necessary to complete the suturing procedure.

The needle loading system 100 preferably includes a suture 107 (not visible in FIG. 3A) that is removably coupled with the needle 101 (e.g., the suture 107 can be cut using endoscopic scissors). In various embodiments, the needle 101 and the needle cover 102 may together form a replaceable cartridge that is delivered to, and removed from, the delivery housing 109 using the loading tool 105. The needle 101, suture 107, needle cover 102, and/or loading tool 105 may form a needle loading system 100 kit. The loading tool 105 and/or the needle cover 102 may be formed from plastic, metal, fiberglass, glass, or any other non-toxic material. The needle loading system 100 may be used with a variety of suturing devices, including the suturing devices described in U.S. patent application Ser. No. 16/433,710, which is incorporated herein by reference in its entirety.

The loading tool 105 is preferably provided pre-coupled with the cover 102 and the needle 101 in the assembled configuration. In various embodiments, the tool 105 holds the needle 101 as it contacts the needle cover 102. However, in some embodiments, the needle cover 102 may additionally, or alternatively, hold the needle 101. In FIG. 3A, the loading system 100 is shown immediately prior to coupling with the suturing device (e.g., the delivery housing 109).

Figure 9:
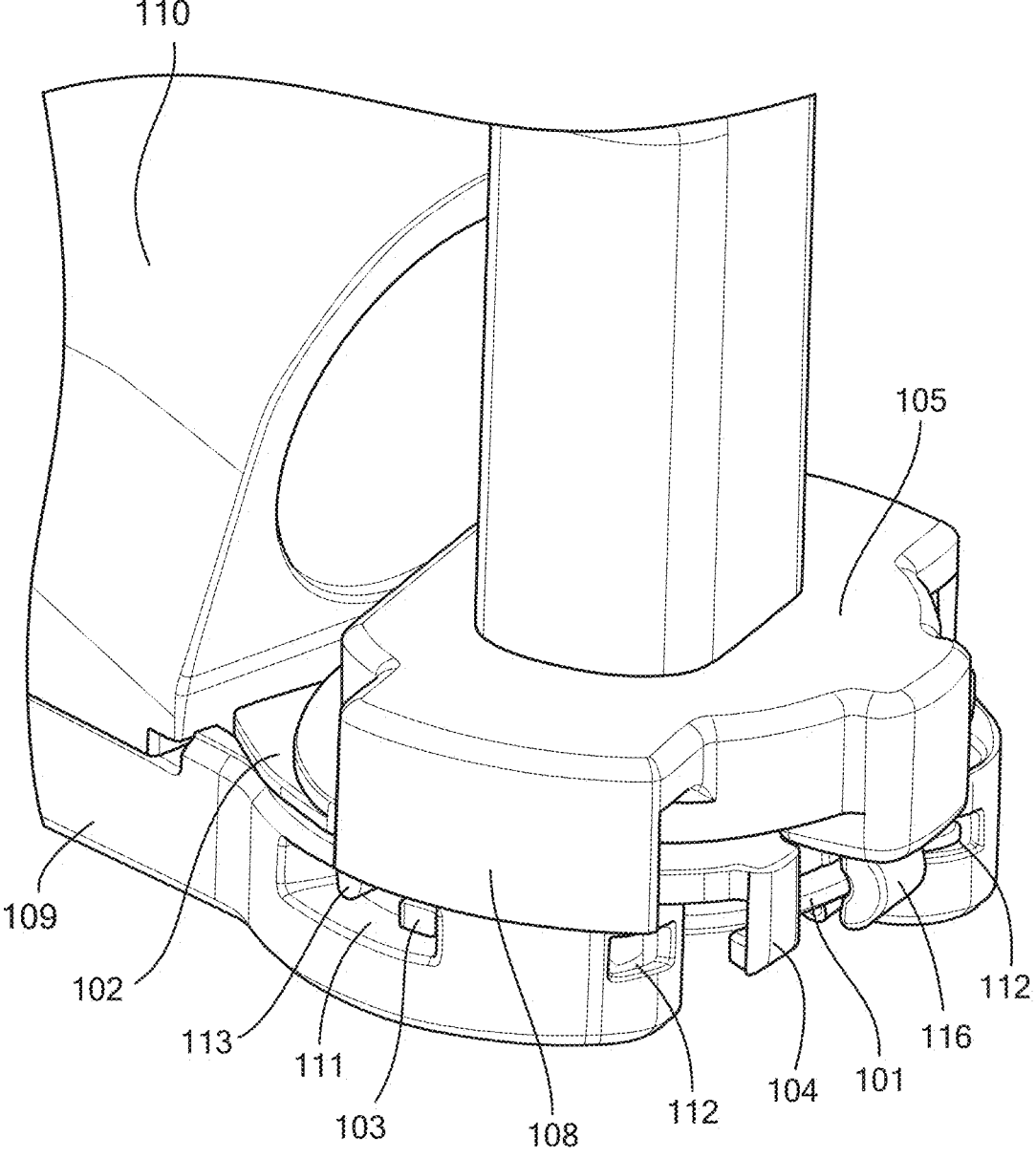
FIG. 9 depicts the needle loading system as it first engages with the delivery housing and endoscope cap before it is turned clockwise and secured into place in accordance with illustrative embodiments of the invention.
Figure 10:
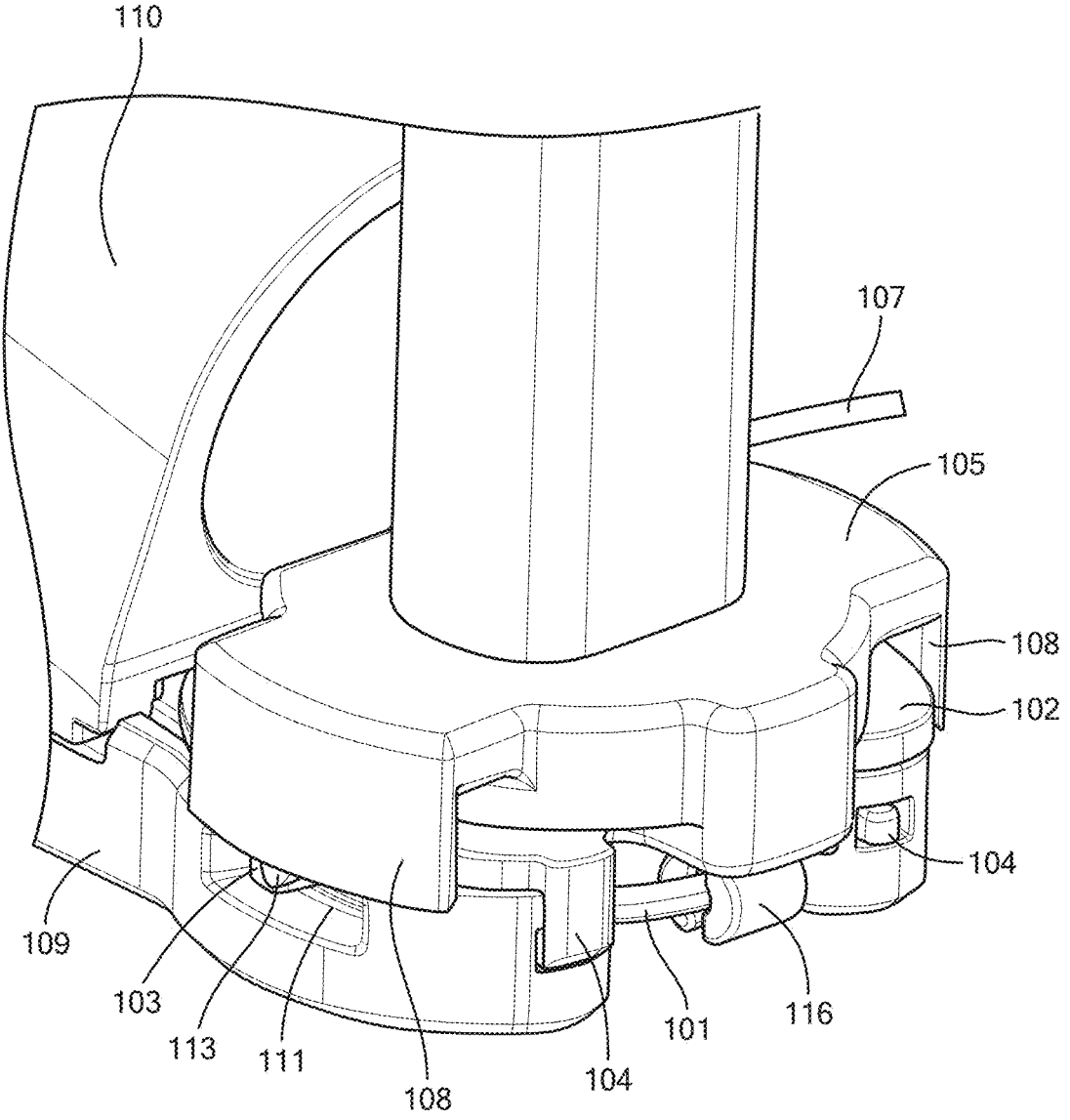
FIG. 10 depicts a needle loading system as it is engaged and secured into a delivery housing and endoscope cap in accordance with illustrative embodiments of the invention.
Figure 11:
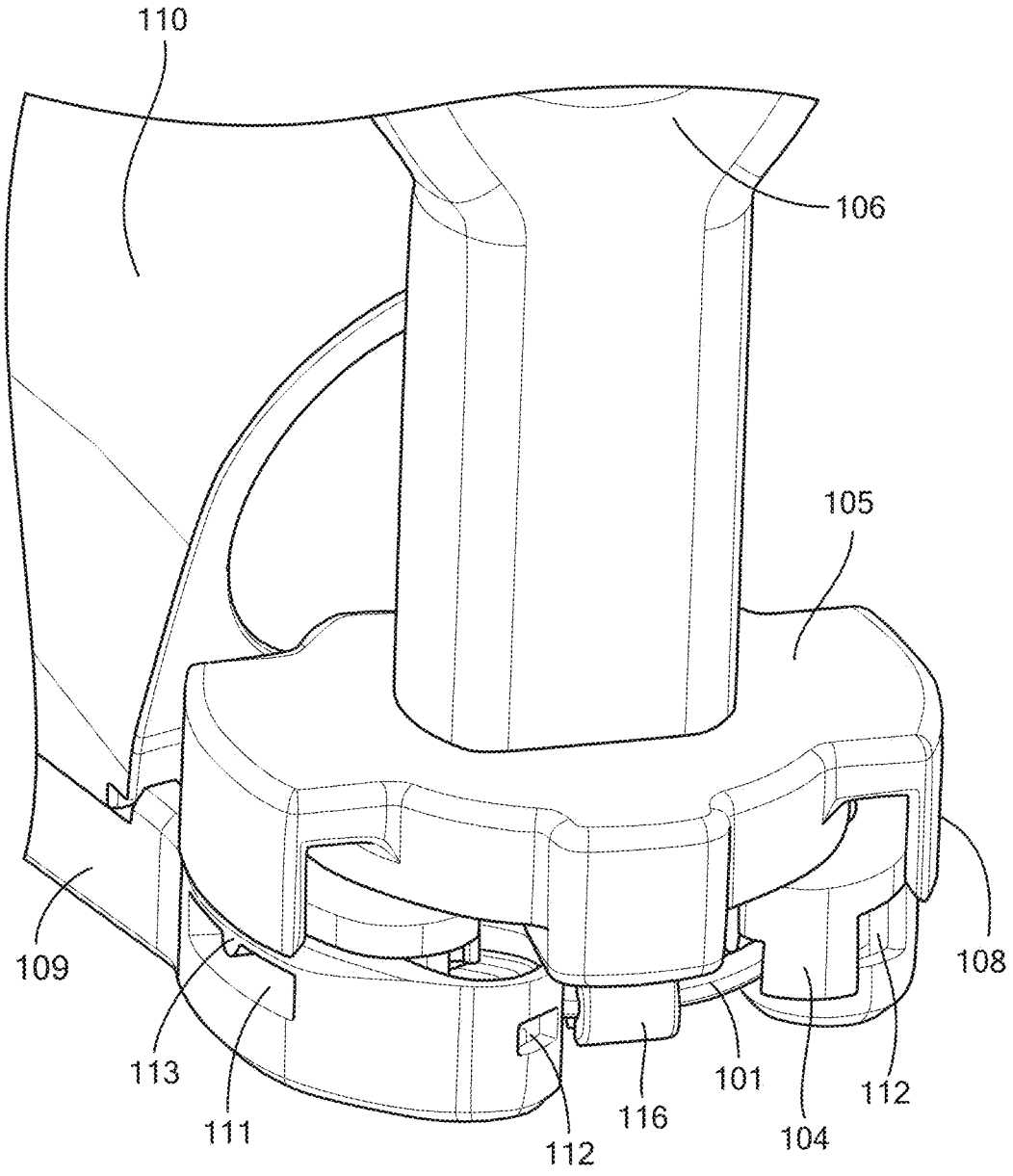
FIG. 11 depicts an alternative configuration to FIG. 9 wherein the needle loading system is rotated counterclockwise to secure in accordance with illustrative embodiments of the invention.
Figure 12:
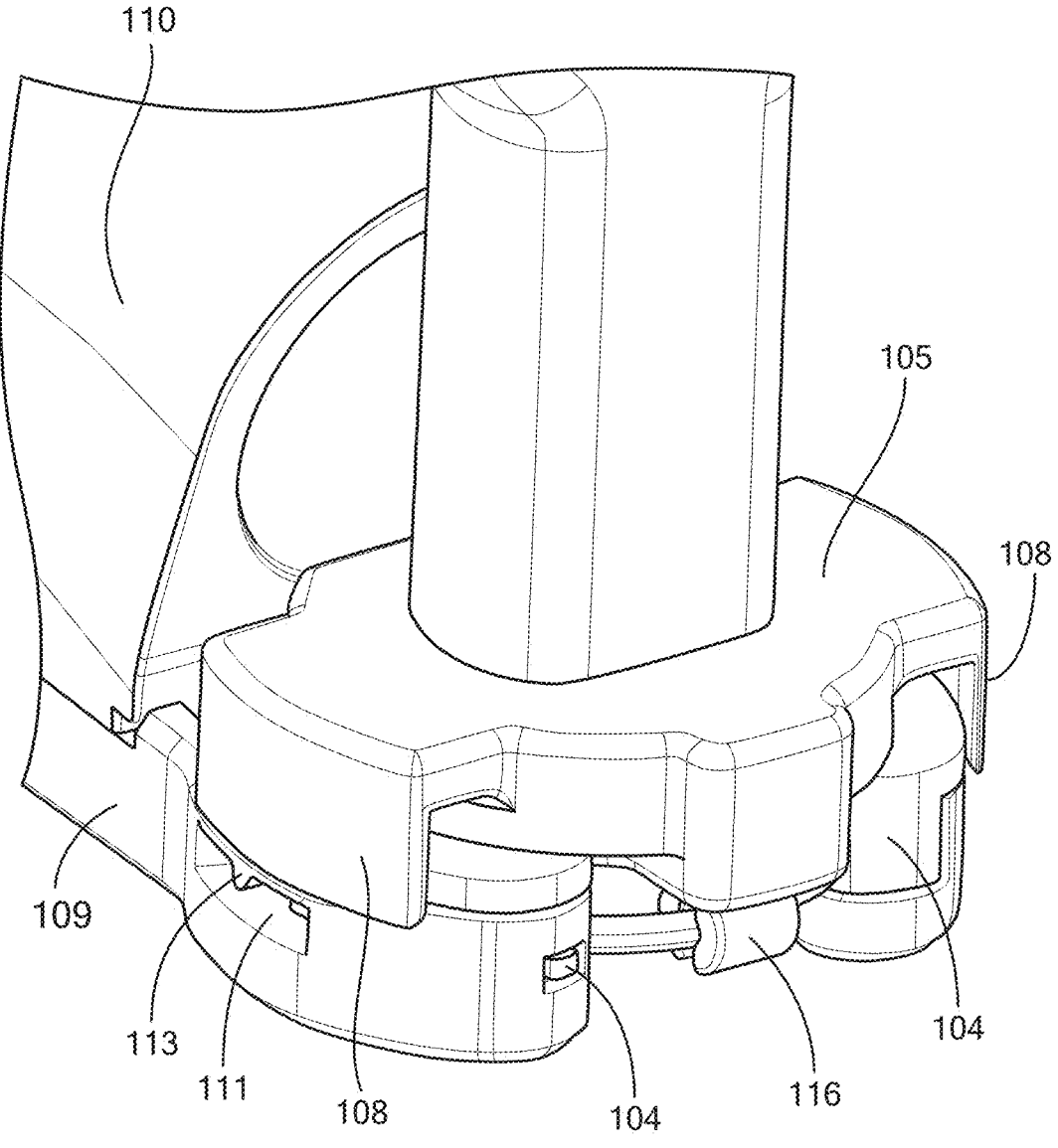
FIG. 12 depicts an alternative configuration to FIG. 10 wherein the needle loading system has been rotated counterclockwise and secured into the delivery housing in accordance with illustrative embodiments of the invention.
Figure 13:
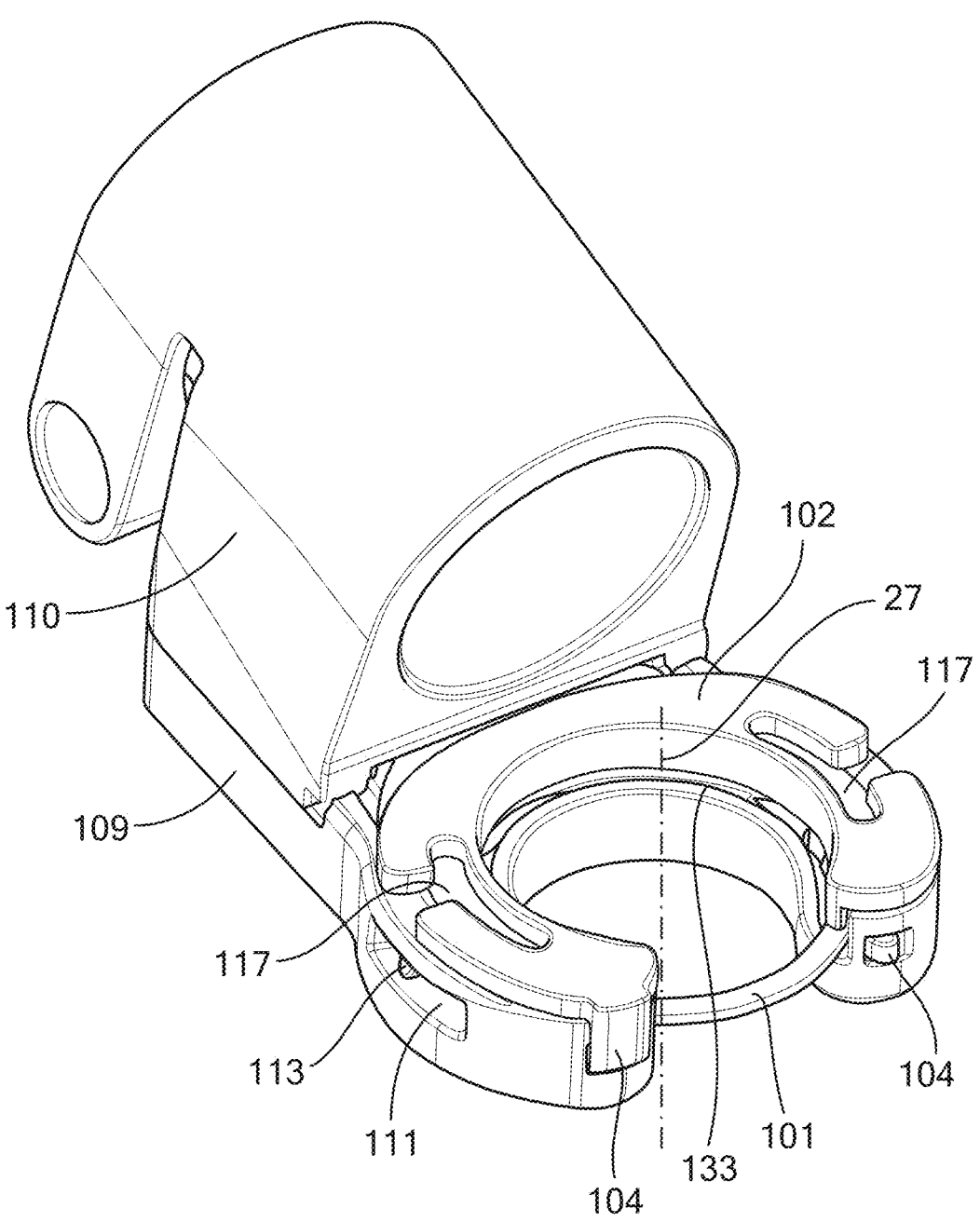
FIG. 13 depicts the needle cover and needle as placed in the delivery housing in a delivery configuration with the loading tool removed in a configuration that has been rotated clockwise to be secured in accordance with illustrative embodiments of the invention.

FIGS. 9 and 11 schematically show alternative embodiments of the loading system 100 in an unsecured assembled configuration with the suturing device. FIGS. 10 and 12 schematically show alternative embodiments of the loading system 100 in a secured assembled configuration with the suturing device. After the loading system 100 is in the secured assembled configuration, the loading tool 105 may be removed, and the needle 101, needle cover 102, and suturing device are in a delivery configuration, for example, as shown in FIG. 13.

Figure 3B:
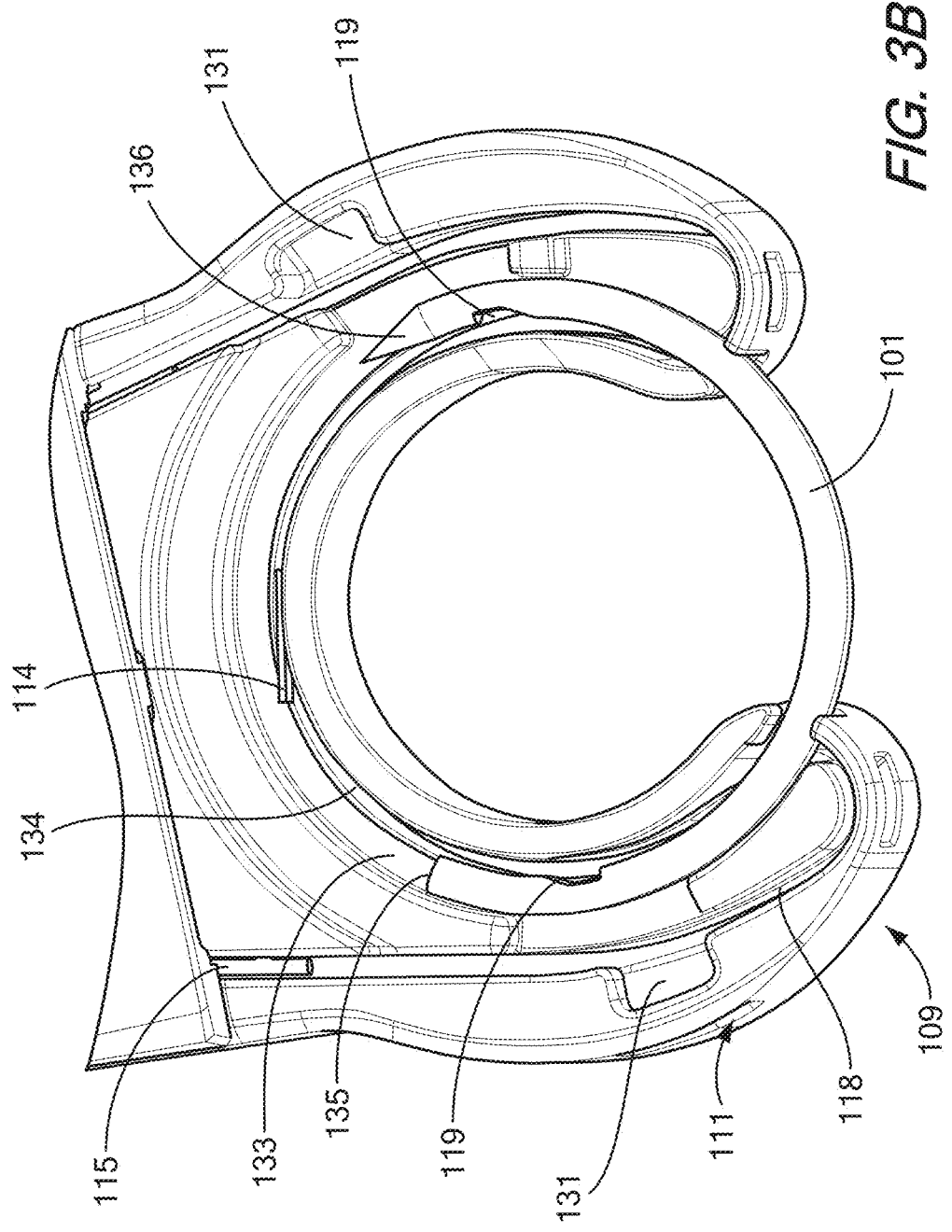
FIG. 3B depicts an exposed view of the needle positioned within a needle track of the delivery housing in accordance with illustrative embodiments of the invention.

To couple the loading system 100 and the delivery housing 109, the loading tool 105 is aligned with the delivery housing 109. Among other ways, the needle 101 substantially aligns with a needle track 133 of the housing 109. Furthermore, side tabs 103 may align with an opening 131 in the side slots 111. As best shown in FIG. 3B, the delivery housing 109 includes openings 131 to allow the side tabs 103 to be positioned within the side slots 111.

The needle loading system 100 is positioned onto the delivery housing 109. In various embodiments, the delivery housing 109 has side slots 111 and front slots 112 that engage corresponding side tabs 103 and front tabs 104, respectively. The side slots 111 and the front slots 112 may include a snap, groove, pin, slot, tab, channel, flexure, detent, or any combination thereof. After the needle cover 102 is positioned onto the delivery housing 109, the medical professional 14 rotates the loading tool 105 by manipulating (e.g., grasping and twisting) the loading tool handle 106. The needle cover 102 and the needle 101 rotate with the loading tool 105. The side tabs 103 rotate within the side slots 111. By pressing down 25A on the needle loading system 100 while rotating, the side tab 103 may rotate under and past a side slot protrusion 113, securing the side tab 103 in the delivery housing 109. The front tabs 104 are also rotated into the front slots 112. Alternatively, or additionally, the front tabs 104 may secure into the front slots 112. Alternatively, or additionally, the side tabs 103 may not secure into the side slots 111. Alternatively, or additionally, the tabs 103, 104 may flex into the slots 111, 112 without being rotated. The needle cover 102 is now secured to the delivery housing 109.

The medical professional 14 may then remove the loading tool 105 by pulling it in an upward direction 25B to uncouple the loading tool 105 from the needle cover 102 and the needle 101. The suturing system is now in the delivery configuration for deployment into a patient 12. Upon completion of the medical procedure, or if the sutures 107 need to be replaced, the medical professional 14 may remove the endoscope 18 from the patient 12 and recouple the loading tool 105 with the needle cover 102 and/or the needle 101 (e.g., by flexing the arms 108 back into engagement with the needle cover).

In the unsecured assembled configuration (i.e., the needle cover 102 is coupled with the tool 105), rotating the loading tool 105 may also rotate the needle cover 102. During rotation, the side tabs 103 of the needle cover 102 rotate under and past the slot protrusion 113. Furthermore, the front tabs 104 are ejected from the front slots 112, thereby unsecuring the needle cover 102 from the delivery housing 109. After the cover 102 is unsecured, the needle loading system 100, including the loading tool 105, the needle cover 102, the needle 101, and/or the remaining suture 107, may be removed from the delivery housing 109 (e.g., to be replaced or to complete the medical procedure).

FIG. 3B depicts an exposed view of the needle 101 positioned within the needle track 133 of the delivery housing 109 in accordance with illustrative embodiments of the invention. In this view, the needle cover 102 and suture

107 are omitted for clarity. However, it should be understood that various embodiments may include the needle cover 102 over the needle 101. As the medical professional 14 sutures a wound, the arcuate needle 101 moves around the needle track 133. To that end, the needle 101 has a tip 136, and a suture attachment end 135. Although not shown in FIG. 3B, the suture attachment end 135 couples with the suture, which may ultimately uncouple from the needle 101 and be left inside of the patient 12. As described further below, the loading tool 105 may be used to remove the needle 101 and the needle cover 102. In various embodiments, an entirely new needle loading system 100 is then provided with a new suture 107 if additional suturing is desired.

The needle 101 engages a drive mechanism of the suturing device, such as a cable or drive belt 118, that controls operation and movement of the needle 101 during the medical procedure. The medical professional 14 may control the drive belt 118 by using pull wire(s) 115. The delivery housing 109 may include a cable track 134 that is at least partially concentric with the needle track 133. When the drive belt 118 and the needle 101 are engaged (e.g., by an upwardly extending pawl 114 and a corresponding needle notch 119), motion of the drive belt 188 moves the needle 101. When the drive belt 118 and the needle 101 are not engaged, they move independently of one another. The operation of the drive belt 118, and alternative embodiments thereof, are described in more detail in U.S. patent application Ser. No. 16/433,710, which is incorporated by reference, in its entirety, herein.

Figure 4:
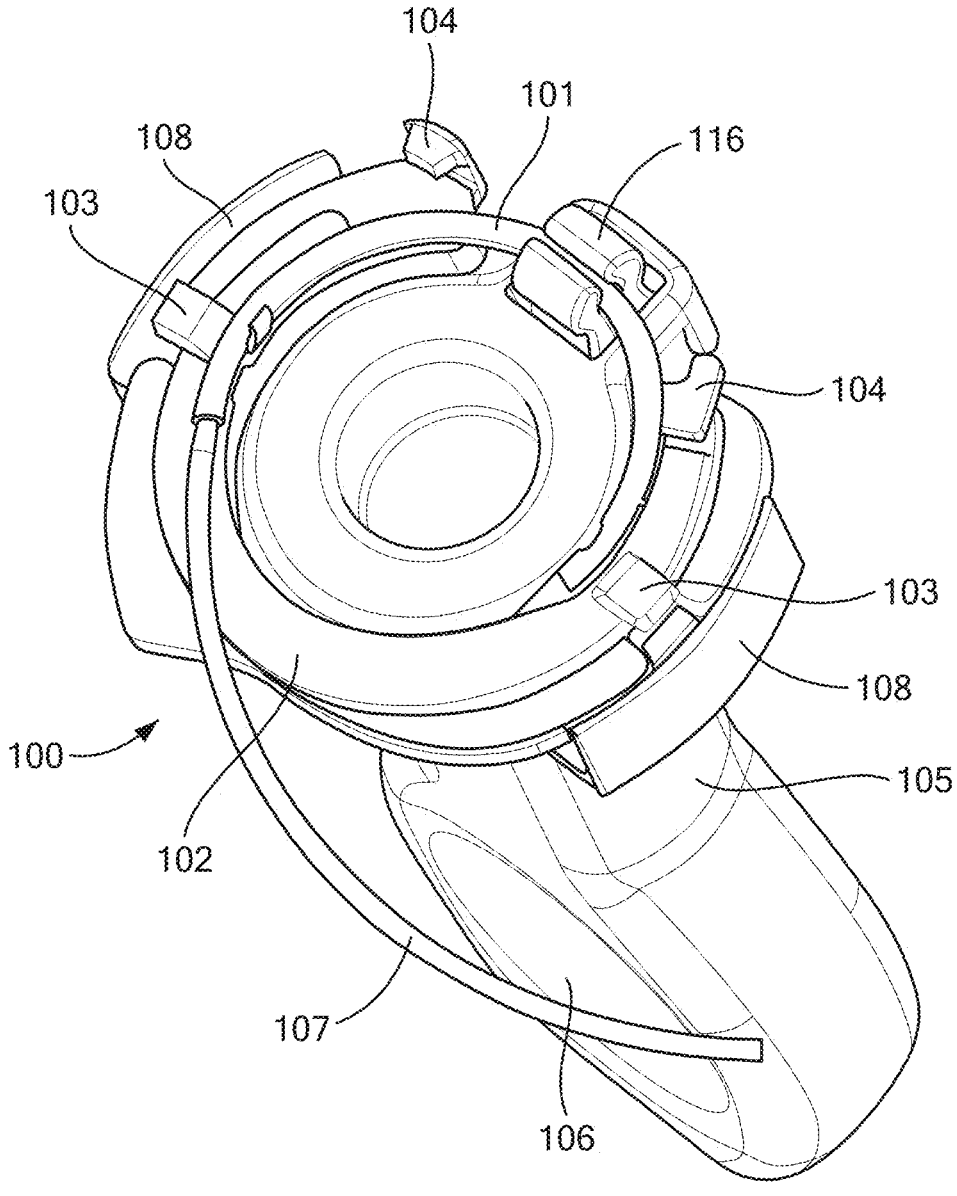
FIG. 4 depicts a bottom view of the needle loading system in accordance with illustrative embodiments of the invention.

FIG. 4 schematically shows a bottom view of the needle loading system 100 in the assembled and primed configuration in accordance with illustrative embodiments. The loading tool 105, the needle cover 102, and the needle 101 are coupled. In illustrative embodiments, the loading tool 105 holds the arcuate needle 101, which is coupled with the suture 107. The needle cover 102 may have one or more tabs (e.g., on the side tabs 103 and front tabs 104) with respect to a front face of the device. In various embodiments, the tabs 103, 104 secure the needle cover 102 to the delivery housing 109. The needle cover 102 is depicted assembled with the loading tool 105. In some embodiments, the loading tool 105 couples with the needle cover 102 using one or more arms 108 on the loading tool 105 (e.g., that "snap onto" or flex over and past the edges of the needle cover 102). The arms 108 are flexible to couple and uncouple with (e.g., flex on and off of) the needle cover 102. However, those skilled in the art can envision a number of other ways to couple the needle cover 102 and the loading tool 105.

In various embodiments, the loading tool 105 includes a needle coupling portion 116 (e.g., a needle coupling portion 116 or other clamp) that holds the arcuate needle 101. The handle 106 allows the medical professional 12 to position the needle loading system 100 into place relative to the delivery housing 109 and subsequently remove the loading tool 105. Upon securing the needle cover 102 into the delivery housing 109 and removing the loading tool 105, the needle loading system 100 is in the delivery configuration and may be deployed into the patient 12. Upon completion of the medical procedure or if the needle 101 and suture 107 are to be replaced, the endoscope 18 is removed from the patient 12. The loading tool 105 is recoupled with the needle cover 102 and/or the needle 101 and may rotate to unlock the needle cover 102 from the delivery housing 109. The medical professional 14 then disengages the loading tool 105 from the delivery housing 109 to remove the needle cover 102 and the needle 101 from the endoscope 18. A different needle loading system 100 may then be applied to the endoscope 18 or the procedure may be completed.

Although various embodiments show that the needle 101 is held by the loading tool 105, in alternative embodiments the needle coupling portion 116 may be additionally, or alternatively, part of the needle cover 102.

Figure 5:
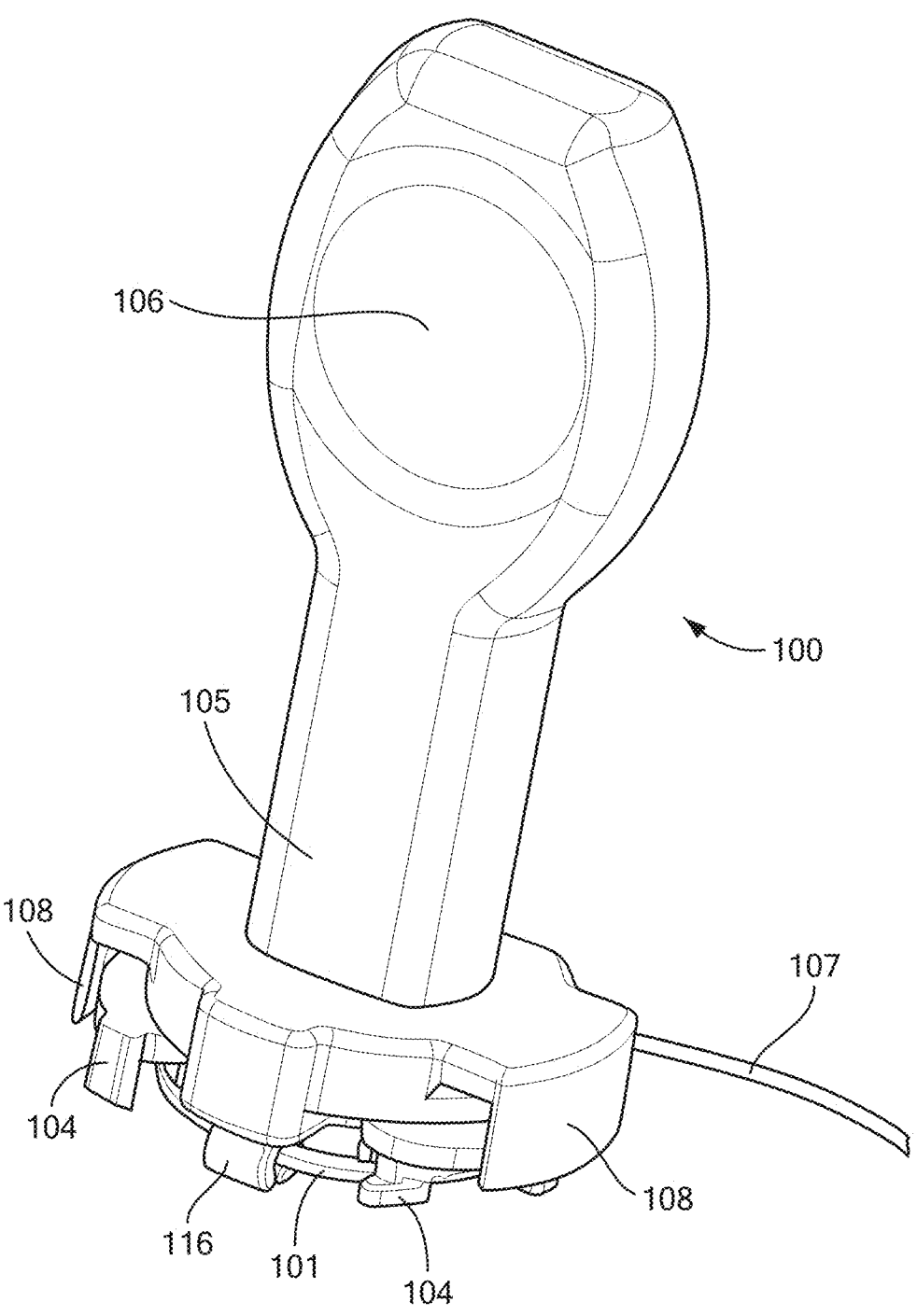
FIG. 5 depicts a front view of the needle loading system in accordance with illustrative embodiments of the invention.

FIG. 5 schematically shows a perspective front view of the needle loading system in the assembled configuration in accordance with illustrative embodiments. The arcuate needle 101 and suture 107 are housed in a needle cover 102, which together form a replaceable package or cartridge. The needle cover 102 includes front tabs 104 and side tabs 103 that are capable of securing the needle cover 102 into the delivery housing 109. The resilient tabs 103, 104 may flex directly into place in the delivery housing 109 or may simply rotate into place by pressing down on the loading tool 105 and rotating the needle cover 102 by rotating the handle 106 to secure. Thus, various embodiments may provide a tactile feel to a medical professional 14 when the delivery housing 109 and the loading tool 105 are coupled. The loading tool 105 has arms 108 that engage the needle cover 102 so that the needle cover 102 rotates with the loading tool 105.

The needle coupling portion 116 couples with the needle 101, keeping the needle 101 in the assembled configuration (e.g., during shipping). The needle 101 may rotate with the loading tool 105 while coupled to secure into the securely primed and/or delivery configuration. The arms 108 and needle coupling portion 116 are flexible and may flex around the edges of the needle cover 102 and/or the needle 101, holding the needle cover 102 and needle 101 in place within the loading tool 105. When the needle cover 102 is secured into place in the delivery housing 109, the medical professional 14 may pull up on the loading tool 105 to cause the corresponding arms 108 of the device to overcome the interference with the cover 102. Accordingly, the loading tool 105 is removed from the needle cover 102 and needle 101 so that the suturing system 100 is in the delivery configuration.

Upon completion of the medical procedure or when the suture 107 and needle 101 need to be replaced, the medical professional 14 may press down the loading tool 105 onto the needle cover 102 and the needle 101. As the loading tool 105 presses down, the arms 108 flex around the edges of the needle cover 102. In a similar manner, the needle coupling portion 116 flexes around the edges of the needle 101, so that the needle loading system 100 is in the secured unprimed configuration. The loading tool 105, cover 102, and/or needle 101 may then rotate (i.e., to the unsecured unprimed configuration) and uncouple from the delivery housing 109 to the assembled configuration. When removing and replacing the loading tool 105, the resilient arms 108 may attach to the needle cover 102 by way of friction fit or by flexing into place. In some instances the needle 101 may not align with the needle coupling portion 116. The medical professional 14 may couple the loading tool 105 with the needle cover 102 without engaging the needle 101. The medical professional 14 may remove the needle cover 102 by rotating the needle loading tool 105 and then separately remove the needle 101. However, in various embodiments, it is preferable that the needle 101 be aligned with the needle coupling portion 116 for easy removal. The loading tool 105 may indicate to the medical professional 14 that it is properly in place through audio, tactile, and/or visual cues. For example, when the loading tool 105 couples with the needle 101, a tactile sensation may be felt at the handle 106.

Figure 6A:
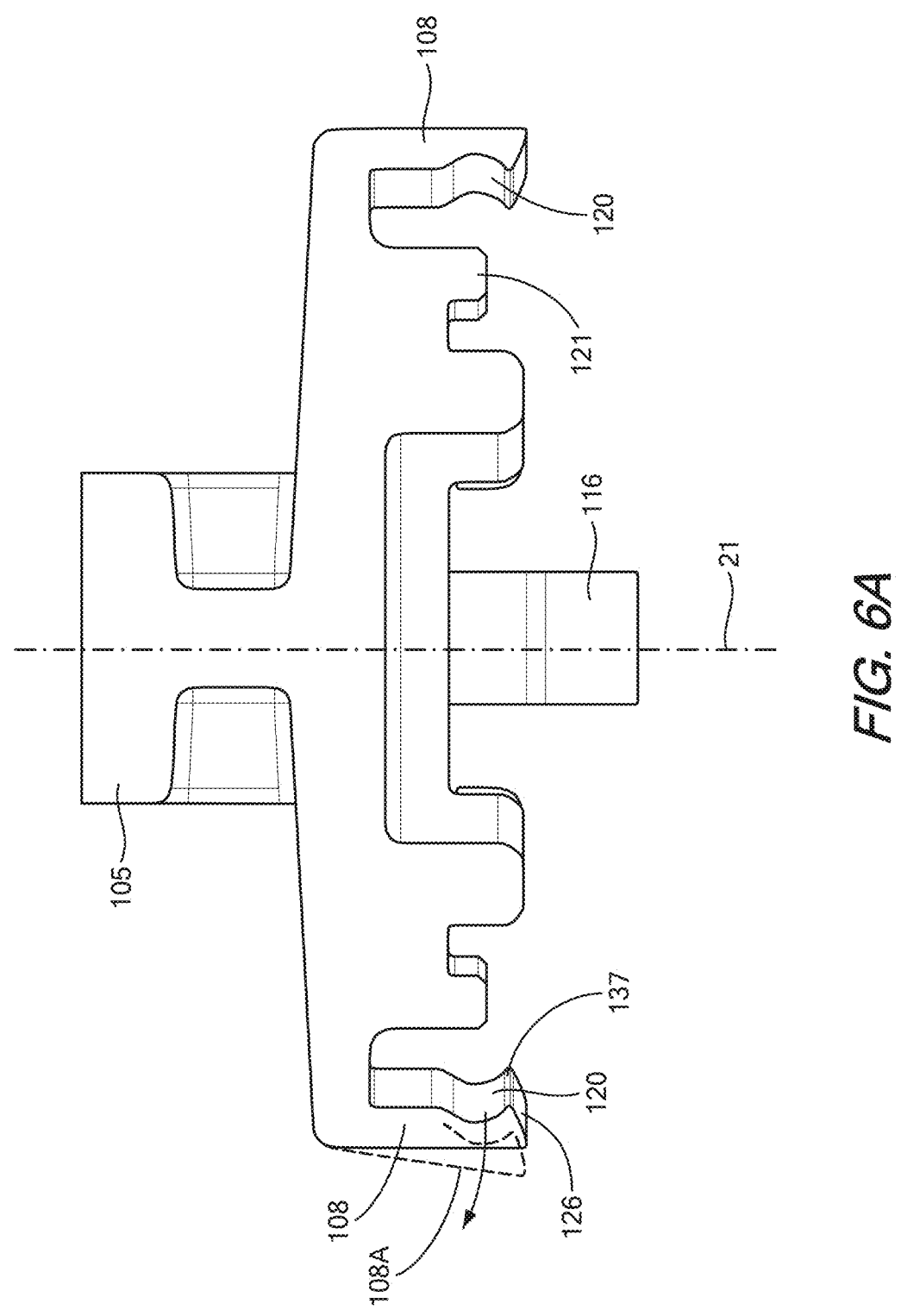
FIG. 6A depicts a close view of the bottom of the loading tool that secures on to a needle cover and needle in accordance with illustrative embodiments of the invention.

FIG. 6A schematically shows a more detailed view of a distal end of the loading tool 105 that engages with the needle 101 and/or the needle cover 102 in accordance with illustrative embodiments. The arms 108 hold the outer edge 123 of the needle cover 102. In various embodiments, the needle cover 102 is positioned within a cover receiving portion 120. A radially inwardly projecting portion 137 of the arms 108 holds the needle cover 102. The arms 108 may include a tapered or beveled surface 126 that makes initial contact with the outer edge of the cover 102. The tapered surface 126 slides along the outer edge of the needle cover 102 and causes the arms to expand outwardly. Thus, the tapered surface 126 allows the arms 108 to flex around the edges of the cover 102. The cover 102 settles into the curved cover receiving portion 120 and the resilient arms 108 spring back and hold the cover 102.

In some other embodiments, the arms 108 may also hold the needle cover 102 by friction fit (e.g., without the use of the cover receiving portion 120). The loading tool 105 also includes the needle coupling portion 116 that engages the needle 101. The arms 108 and the needle coupling portion 116 maintain the needle 101 and needle cover 102 in the assembled configuration. By holding or fitting through friction fit, the loading tool 105 is rotatably coupled with the needle 101 and the needle cover 102. Thus, the medical professional 14 may rotate the loading tool 105, and the needle cover 102 and needle 101 rotate with the loading tool 105. In various embodiments, the needle cover 102 is secured to the delivery housing 109 by rotating the tool 105. To transition the device into the delivery configuration for deployment into the patient 12, the tool 105 may be removed.

Figure 6B:
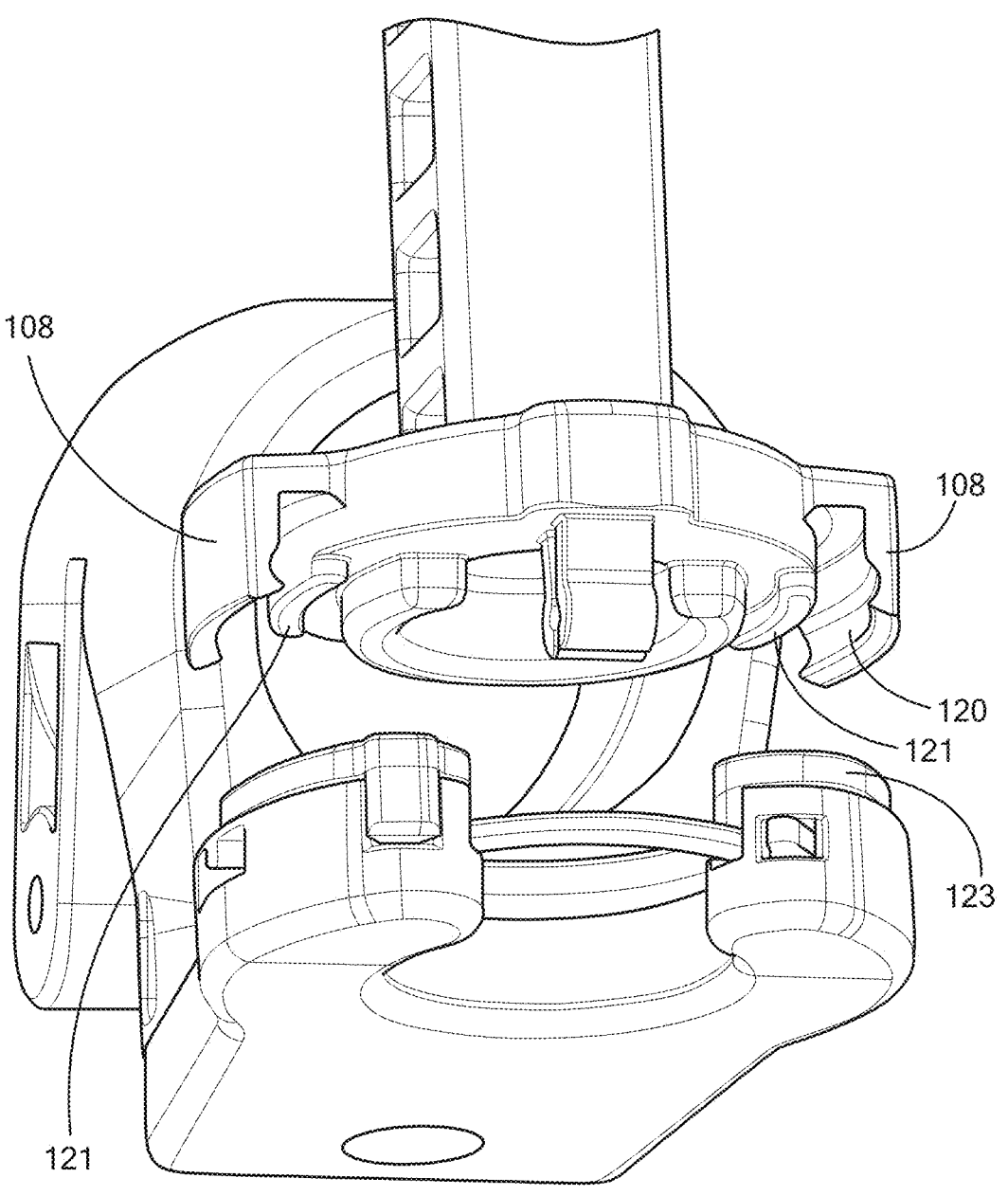
FIGS. 6B-6C depict additional details of alignment of the tool with the cover in accordance with illustrative embodiments of the invention.
Figure 6C:
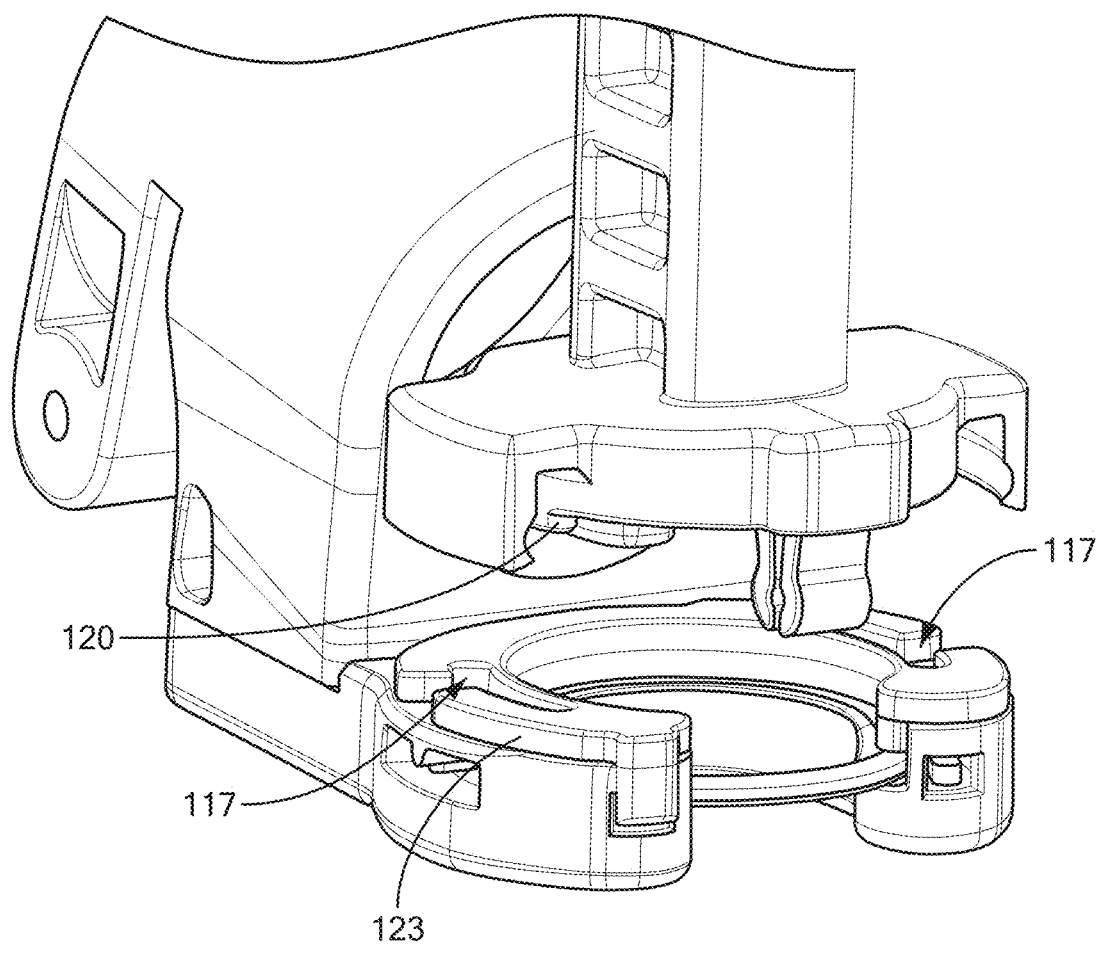

FIGS. 6B-6C schematically show additional details of alignment of the tool 105 with the cover 102 in accordance with illustrative embodiments of the invention. As the medical professional presses the loading tool 105 on the needle cover 102, the arms 108 flex outwardly to accommodate the edges of the needle cover 102 (e.g., shown by phantom arm 108A in FIG. 6A). The outer edge 123 is positioned within the cover receiving portion 120. Additionally, one or more projections 121 (e.g., on the tool 105) may be positioned within one or more counterpart recess 117 of the cover 102. This helps to align the cover 102 with the tool 105 for coupling, and additionally supports rotational coupling for securing and unsecuring the cover 102 to and from the delivery housing 109. In some embodiments, the projections 121 may be on the tool, the cover, or both, and counterpart recesses 117 may be on the tool, the cover, or both.

After the needle cover 102 is secured to the delivery housing 109, as the user pulls up the loading tool 105, the arms 108 may again flex outwardly and pass around the edges 123 of the needle cover 102 to uncouple the loading tool 105 with the needle cover 102. Additionally, the projections 121 may be removed from the recesses 117 by pulling the tool 105 away from the cover 102. This allows the device to transition from the secured coupled configuration to the delivery configuration for deployment into the patient 12. The use may align and press down the tool 105 on the cover 102 to couple them together. The tool may then be used for unsecuring the cover 102, and also for removing the cover 102 from the delivery housing 109 and the endoscope 18.

Figure 7:
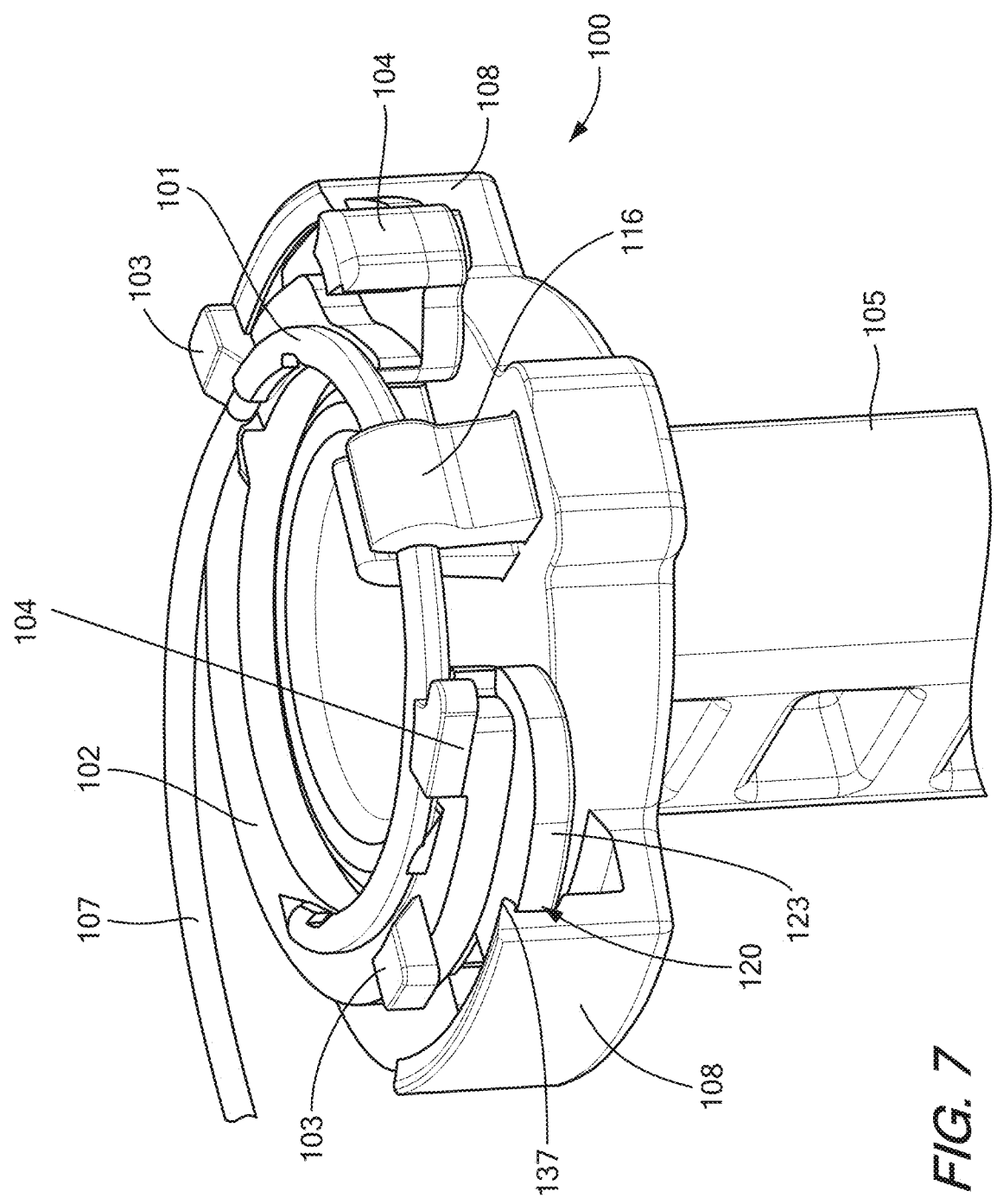
FIG. 7 depicts a bottom view of the loading tool engaged with the needle cover and needle in accordance with illustrative embodiments of the invention.

FIG. 7 schematically shows a bottom view of the needle loading system 100 in accordance with illustrative embodiments. In the coupled configuration as shown in FIG. 7, the arcuate needle 101 and suture 107 are held in the needle cover 102 and by the needle coupling portion 116 of the loading tool 105. Holding the needle 101 in the needle coupling portion 116 and resting on needle cover 102 ensures the needle stays in the assembled configuration until loaded onto the delivery housing 109 on the endoscope 18. The needle cover 102 has corresponding side tabs 103 and front tabs 104 that secure the needle cover into place on the delivery housing 109. The loading tool 105 has a needle coupling portion 116 that holds the needle 101. The loading device also has arms 108 holding the needle cover 102. The needle coupling portion 116 and arms 108 allow the needle 101 and needle cover 102 to rotate with the loading tool 105 to secure the needle cover 102 into the delivery housing 109. The arms 108 and needle coupling portion 116 flex so as to move onto and around the edges of the needle cover 102 and needle 101, respectively. After the needle cover 102 is secured into the delivery housing 109 on the endoscope 18 to the suturing device is in the delivery configuration for deployment into the patient 12. Upon completion of the medical procedure or if the suture 107 needs to be replaced, the endoscope 18 is removed from the patient 12 and the loading tool 105 is recoupled to the needle cover 102 and needle 101 to return to the coupled configuration for easy removal from the delivery housing 109 and endoscope 18.

Figure 8:
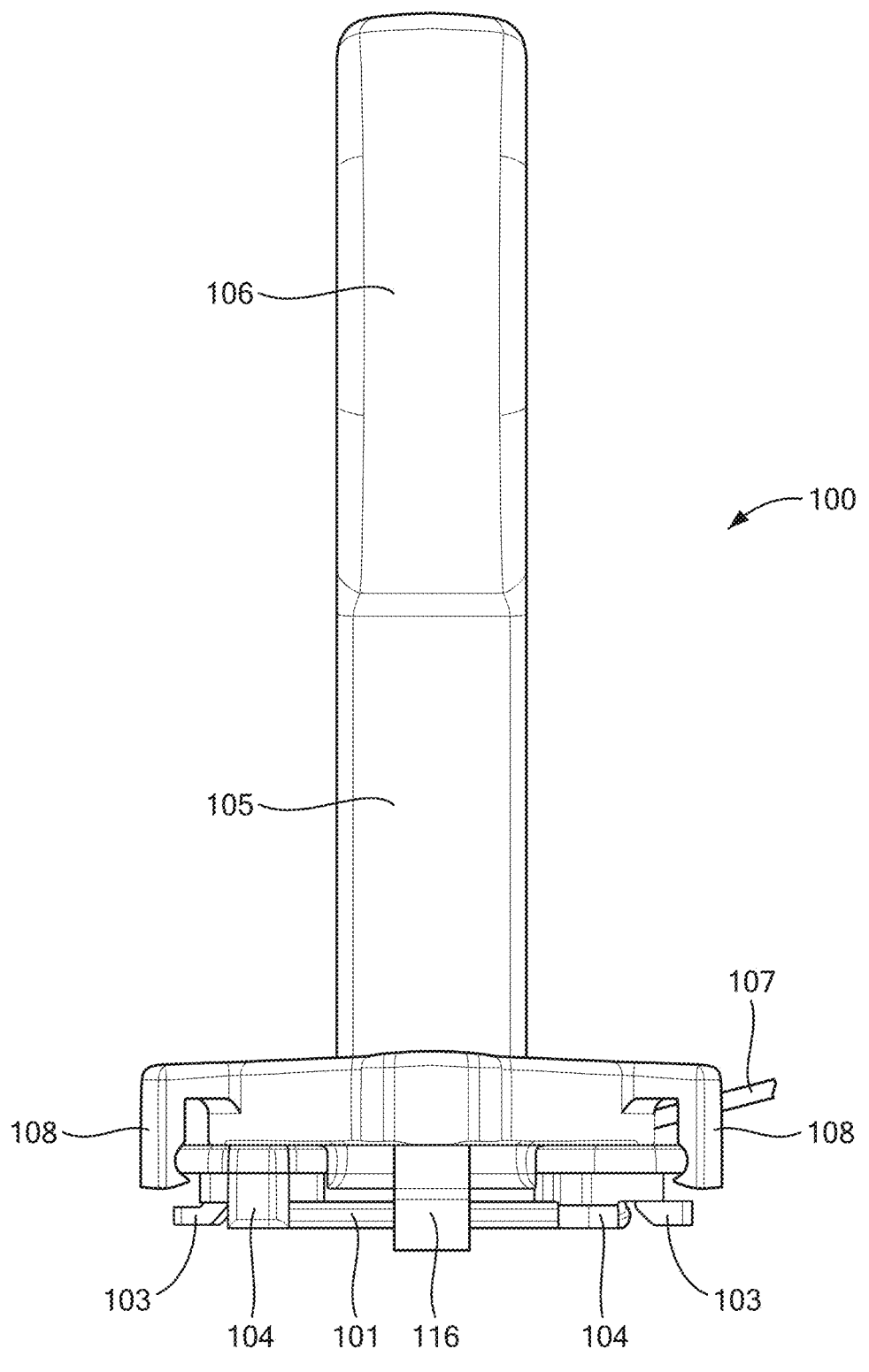
FIG. 8 depicts a side view of the needle loading system with the loading tool engaged with the needle cover and needle in accordance with illustrative embodiments of the invention.

FIG. 8 schematically shows a front view of the needle loading system in the assembled configuration. The loading tool 105 is coupled with the needle cover 102 by arms 108 that clasp the needle cover 102, but may also hold the needle cover 102 by friction fit. The loading tool 105 is coupled with the needle cover 102 in order to maintain the needle cover 102 in the coupled configuration during transport and to rotate the needle cover 102 when the loading tool 105 is rotated in order to secure the needle cover 102 into the delivery housing 109 on the endoscope 18. The needle cover has front tabs 104 and side tabs 103 for securing the needle cover 102 into the delivery housing 109 on the endoscope 18. The tabs 103, 104 may flex to allow the needle cover 102 to be placed into the delivery housing 109. Alternatively, the needle cover 102 may rotate to rotate the tabs 103, 104 into place in the delivery housing 109. The loading tool 105 couples with the needle 101 by a needle coupling portion 116 in order to keep the needle in the assembled configuration during transport and to rotate the needle 101 when the loading tool 105 rotates. A medical professional 14 may grasp the loading tool handle 106 in order to hold the needle loading system and rotate the system.

FIG. 9 schematically shows a needle loading system as engaged with the delivery housing 109 in the unsecured position. The delivery housing 109 is coupled with an endoscope cuff 110 that connects the delivery housing 109 to the distal end of an endoscope 18. After the needle loading system is lowered onto the delivery housing 109, the needle loading system is rotated (e.g., clockwise) to secure the needle cover 102 and needle 101 into the delivery housing 109. The medical professional 14 holds the loading tool 105 by the handle 106 and rotates the loading tool 105 clockwise. The loading tool 105 is coupled with the needle cover 102 by arms 108 that hold the needle cover 102 by flexing around the edges of the needle cover 102. The arms 108 may also fit onto the needle cover 102 by friction fit. The loading tool 105 is also coupled with the needle 101 by a needle coupling portion 116. This ensures the needle 101 and needle cover 102 remain in the coupled configuration during shipping and loading.

In illustrative embodiments, by rotating clockwise, the front tabs 104 slide into the front slots 112 and the side tabs 103 slide into the side slots 111. The side tabs 103 and front tabs 104 may also secure into the delivery housing 109. By pressing down on the loading tool 105 and rotating clockwise, the side tab 103 travels below and past the side slot protrusion 113 in the delivery housing 109, securing the side tab 103 into place. The loading tool 105 may then be removed from the needle 101 and needle cover 102 by pulling up on the loading tool 105, flexing the arms 108 and needle coupling portion 116 off of the needle cover 102 and needle 101. The needle loading system 100 is then in the delivery configuration for deployment into the patient 12. Upon completion of the surgery or if a suture 107 or needle 101 needs to be replaced, the medical professional 14 may remove the endoscope 18 from the patient 12 and recouple the loading tool 105 back onto the delivery housing 102 and needle 101 (e.g., by flexing the arms 108 over the needle cover 102 and flexing the needle coupling portion 116 over the needle 101).

The arms 108 may also engage the needle cover 102 by friction fit. The medical professional 14 may then press down on the loading tool 105 and rotate the needle loading system counterclockwise to unlock the needle loading system from the delivery housing 109. The needle loading system may also rotate without pressing down to unlock the needle loading system from the delivery housing 109. In some embodiments, the drive mechanism for suturing is housed within the delivery housing 109 and remains attached to the endoscope 18. Various embodiments provide for easy removal and replacement of the needle 101 and suture 107 (e.g., any portion that remains after the surgeon cuts the suture with endoscopic scissors). Additionally, various embodiments provide cost-savings over other prior art systems that the inventors are aware of, particularly because various embodiments reuse the delivery housing 109 and drive mechanism.

FIG. 10 schematically shows the needle loading system of FIG. 9 in the secured position in the delivery housing 109. By rotating the needle loading system clockwise, the side tabs 103 are rotated below and past the side slot protrusion 113, securing the needle cover 102 in place in the delivery housing 109. The front tabs 104 slide and may secure into place into the front slots 112. The loading tool 105 may then be removed from the needle loading system, transitioning the system to the delivery configuration for deployment into a patient 12.

FIG. 11 schematically shows the needle loading system of FIG. 9 in the unsecured position, however the needle loading system of FIG. 11 rotates counterclockwise to be secured and clockwise to be unsecured from the delivery housing 109. In order to secure the needle cover 102 into the delivery housing, the medical professional 14 rotates the loading tool 105 counterclockwise to secure the side tabs 103 into the side slots 111, and slide the front tabs 104 into the front slots 112. The loading tool 105 may then be removed from the needle cover 102 by pulling up on the loading tool 105, uncoupling it from the needle cover 102 and needle 101. To unlock and remove the needle cover 102 and needle 101 from the delivery housing 109, the loading tool 105 may recouple with the needle cover 102 by pressing the loading tool 105 onto the needle cover 102 and/or the needle 101. The medical professional 14 then rotates the needle loading system clockwise to unlock the needle cover 102 and/or the needle 101 from the delivery housing 109 and may then remove the needle loading system from the delivery housing 109.

FIG. 12 schematically shows the needle loading system of FIG. 11 in the secured position in the delivery housing 109. By rotating the needle loading system counterclockwise, the side tabs 103 are rotated below and past the side slot protrusion 113, securing the needle cover 102 in place in the delivery housing 109. The front tabs 104 slide and may secure into place into the front slots 112. The loading tool 105 may then be removed from the needle loading system, transitioning the system to the delivery configuration for deployment into a patient 12.

FIG. 13 schematically shows the needle loading system in the delivery configuration with the loading tool 105 removed. The delivery housing 109 is couples with the distal end of an endoscope 18 by an endoscope cuff 110. The delivery housing 109 may also attach directly to the endoscope 18. The needle cover 102 of FIG. 13 has been rotated clockwise and the side tabs 103 are secured into the side slots 111 by the side slot protrusion 113. The front tabs 104 are within the front slots 112. The front tabs 104 and side tabs 103 maintain the needle cover 102 in the delivery configuration on the delivery housing 109. The needle cover 102 has tool coupling portions 117 (e.g., slots or grooves) to hold the loading tool 105 in place on the needle cover in the assembled configuration. The loading tool 105 slides into the top slots 117, attaching the loading tool 105 to the needle cover 102. The needle 101 is able to move along the needle track 133 (e.g., rotate around a central axis 27 that is perpendicular to a plane defined by the needle track 133 and passed through the middle of a circle or semi-circle defined by the needle track 133).

Figure 14:
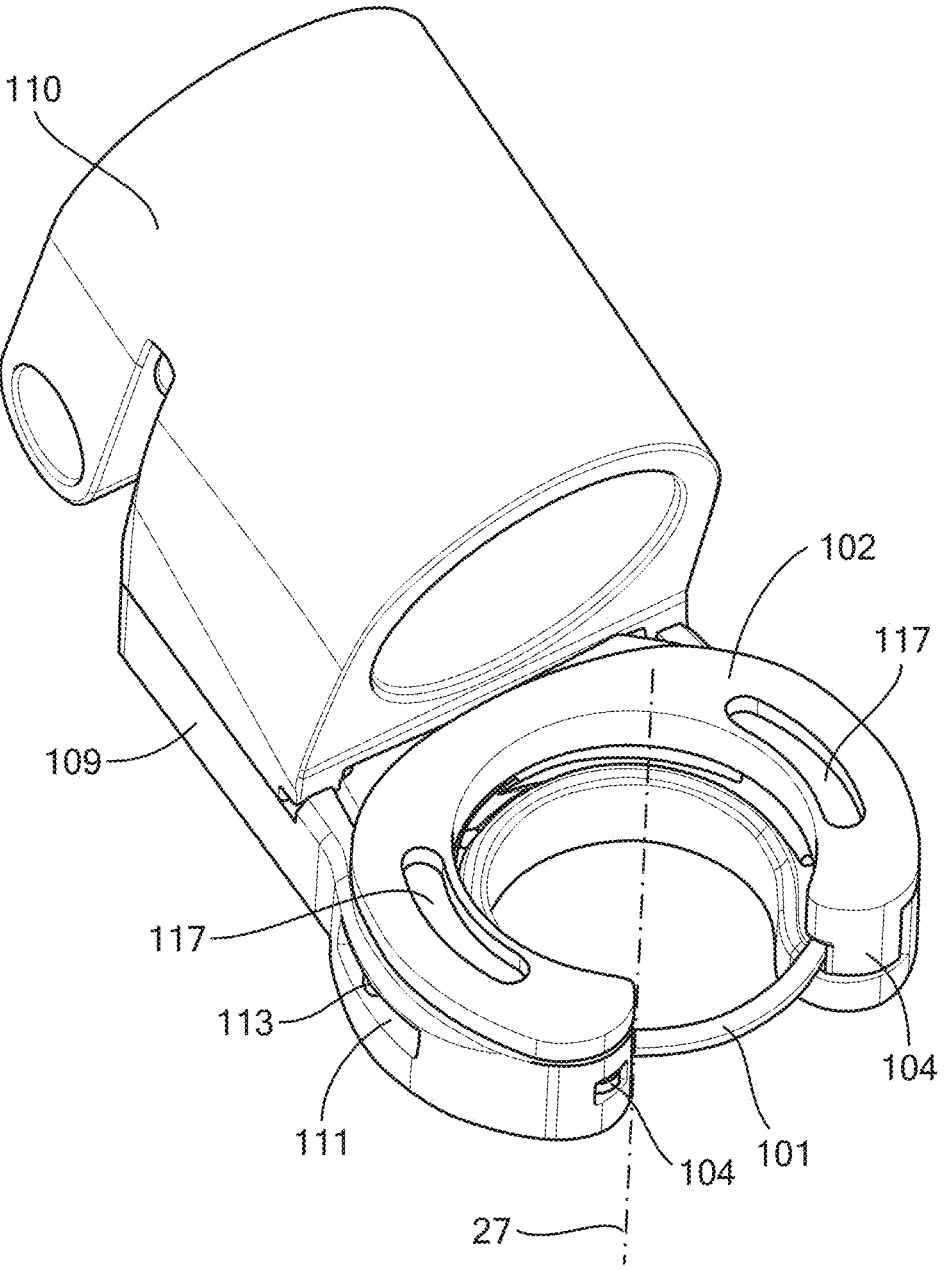
FIG. 14 depicts an alternative configuration to FIG. 13 wherein the needle cover has been rotated counterclockwise to be secured in accordance with illustrative embodiments of the invention.

FIG. 14 schematically shows an alternative embodiment of the needle loading system in the delivery configuration with the loading tool 105 removed. The delivery housing 109 is coupled with the distal end of an endoscope 18 by an endoscope cuff 110. The delivery housing 109 may also be attached directly to the endoscope 18. The needle cover 102 of FIG. 14 has been rotated counterclockwise and the side tabs 103 are secured into the side slots 111 by the side slot protrusion 113.

Figure 15:
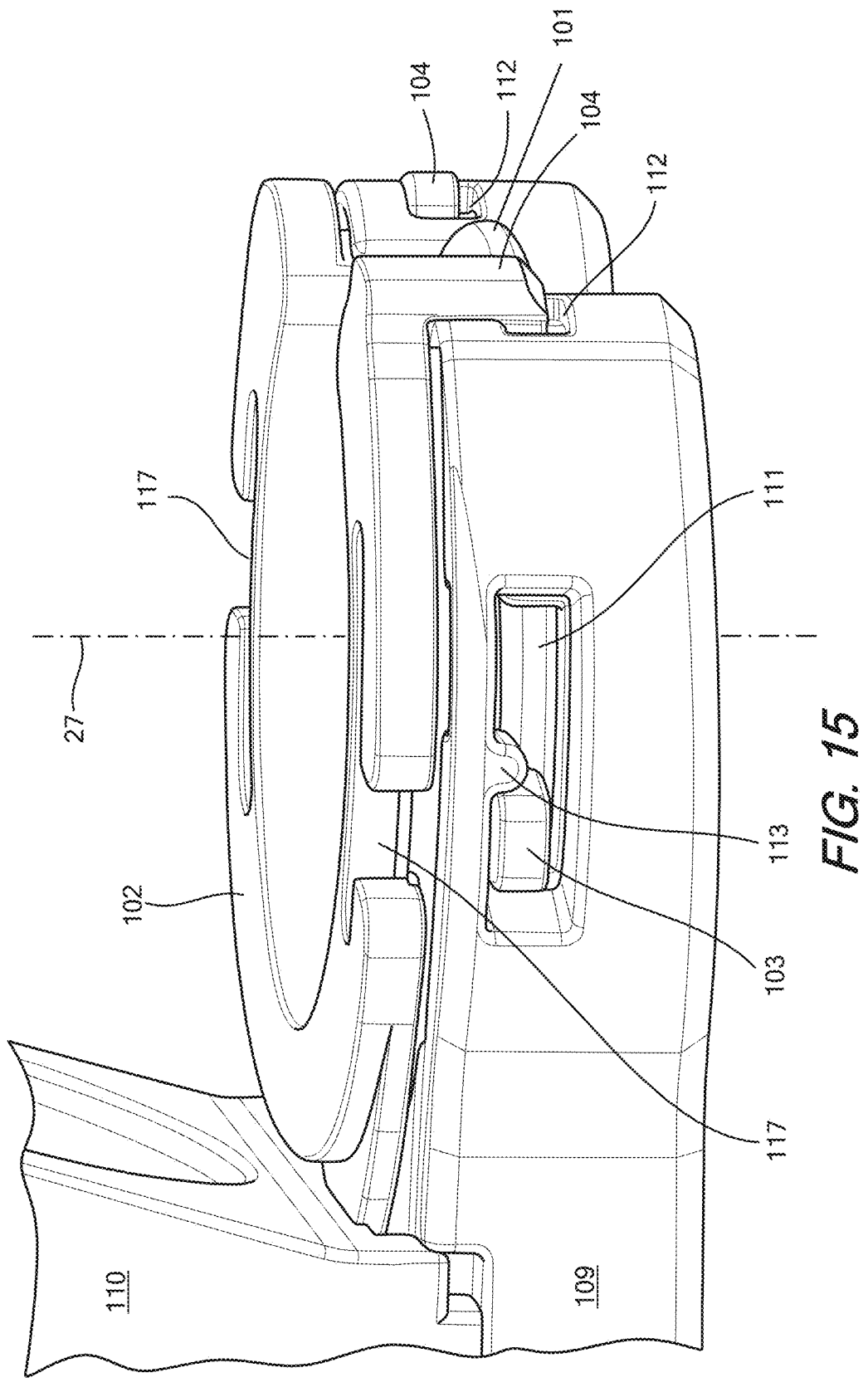
FIG. 15 depicts a side view of the needle cover and needle as secured into a delivery configuration within the delivery housing on the endoscope cap in accordance with illustrative embodiments of the invention.

FIG. 15 schematically shows a side view of the needle cover 102 of FIG. 13 secured into the delivery housing 109 in the delivery configuration. By rotating the needle cover 102, the side tabs 103 slide in the side slots 111 past the side slot protrusion 113 and are secured into place by the protrusion 113. The front tabs 104 slide into the front slots 112, further holding the needle cover 102 in place on the delivery housing 109. By securing the needle cover 102 in place on the delivery housing 109, the needle 101 stays within the delivery housing 109 for delivery into the patient 12 and suturing.

Figure 16:
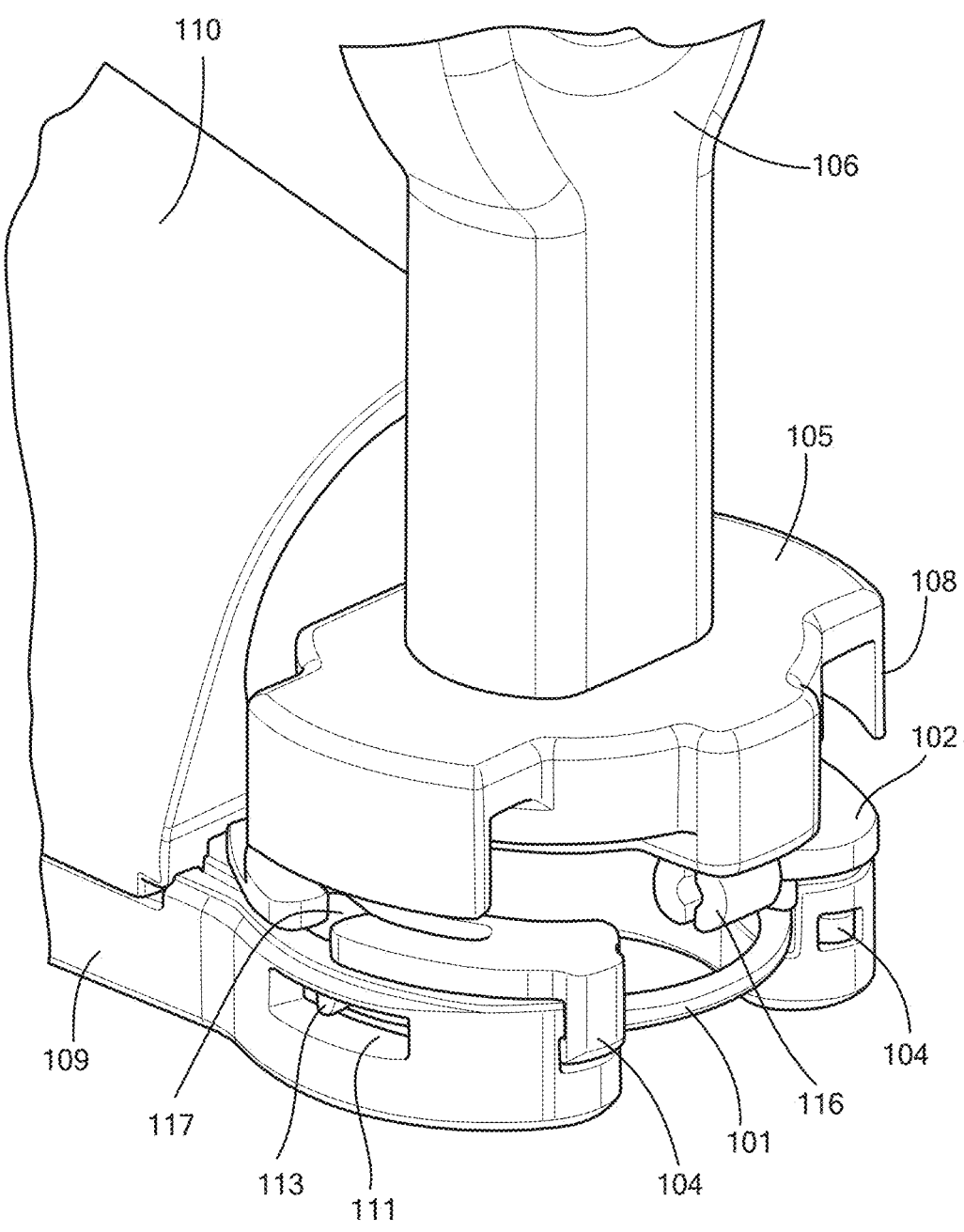
FIG. 16 depicts a view of the loading tool after the needle cover and needle have been secured into the delivery configuration within the delivery housing and the loading tool has been disengaged in accordance with illustrative embodiments of the invention.

FIG. 16 schematically shows the needle loading system in the delivery configuration with the loading tool 105 removed from the needle cover 102 and needle 101. To attach the needle loading system 100 to the delivery housing 109, the medical professional 14 lowers the needle loading system onto the delivery housing 109. The medical professional, holding the handle 106 of the loading tool 105, rotates the loading tool 105 which is coupled with the needle cover 102 using arms 108 and coupled with the needle 101 by a needle coupling portion 116. When the loading tool 105, needle cover 102, and needle 101 are rotated, the side tabs 103 slide in the side slots 111, past the side slot protrusion 113 and secure into place. The front tabs 104 slide into the front slots 112, further securing the needle cover 102 on the delivery housing 109. The loading tool 105 is then removed from the needle 101 and needle cover 102 by pulling up on the loading tool 105, removing the loading tool 105 from the needle cover 102 and needle 101. Upon completion of the medical procedure or if the needle 101 and suture 107 need to be replaced, the medical professional 14 may couple the loading tool 105 onto the needle 101 and needle cover 102. The medical professional 14, grasping the handle 106, may rotate the needle loading system 100, sliding the side tabs 103 past the side slot protrusion 113 and front tabs 104 out of the front slots 112 and unlocking the needle loading system 100. The needle loading system 100 may then be removed from the delivery housing 109 for easy replacement.

Figure 17:
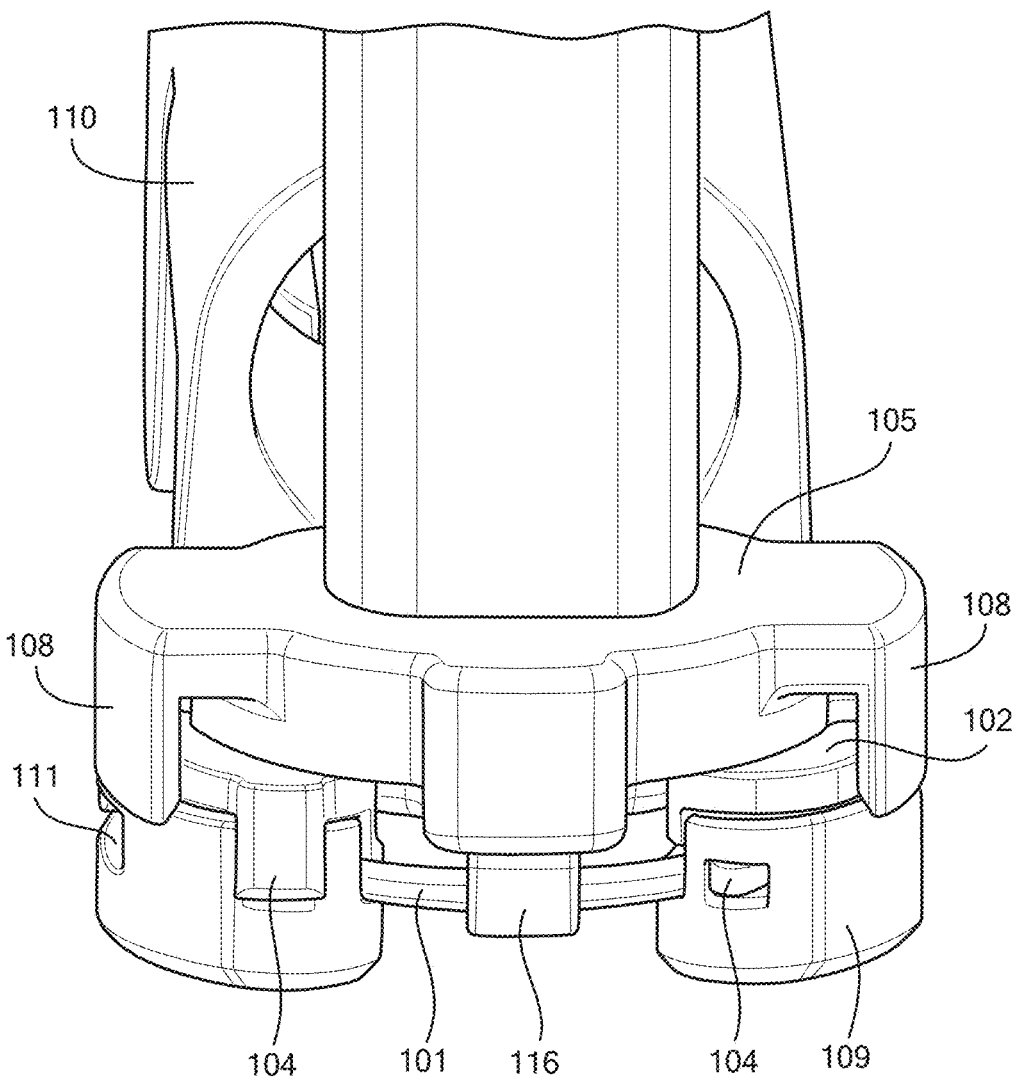
FIG. 17 depicts a front view of the needle loading system as it engages the delivery housing in accordance with illustrative embodiments of the invention.

FIG. 17 schematically shows a front view of the needle loading system 100 in the coupled configuration, secured into the delivery housing 109. In the coupled configuration, the loading tool 105 couples with the needle cover 102 by arms 108 and couples with the needle 101 by a needle coupling portion 116. The loading tool 105 may couple with the needle cover 102 by flexing the arms 108 over the needle cover or by friction fit. The needle loading system 100 lowers onto the delivery housing 109. The medical professional 14 then rotates the needle loading system 100. The side tabs 103 slide in the side slots 111 past the side slot protrusion 113, and front tabs 104 into the front slots 112, securing the needle cover 102 into the delivery housing 109. The loading tool 105 may then be removed from the needle cover 102 and needle 101 by pulling up on the loading tool, therefore transitioning the needle loading system 100 into the delivery configuration. Upon completion of the medical procedure, or if the needle 101 and suture 107 need to be replaced, the medical professional 14 recouples the loading tool 105 onto the needle cover 102 and needle 101. The medical professional then rotates the loading tool 105, rotating the needle cover 102 and needle 101, unlocking the needle cover 102 from the delivery housing 109. After the needle cover 102 is unsecured from the delivery housing 109, the medical professional 14 may pull up on the needle loading system 100, removing it from the delivery housing 109 for easy disposal or replacement.

Figure 18A:
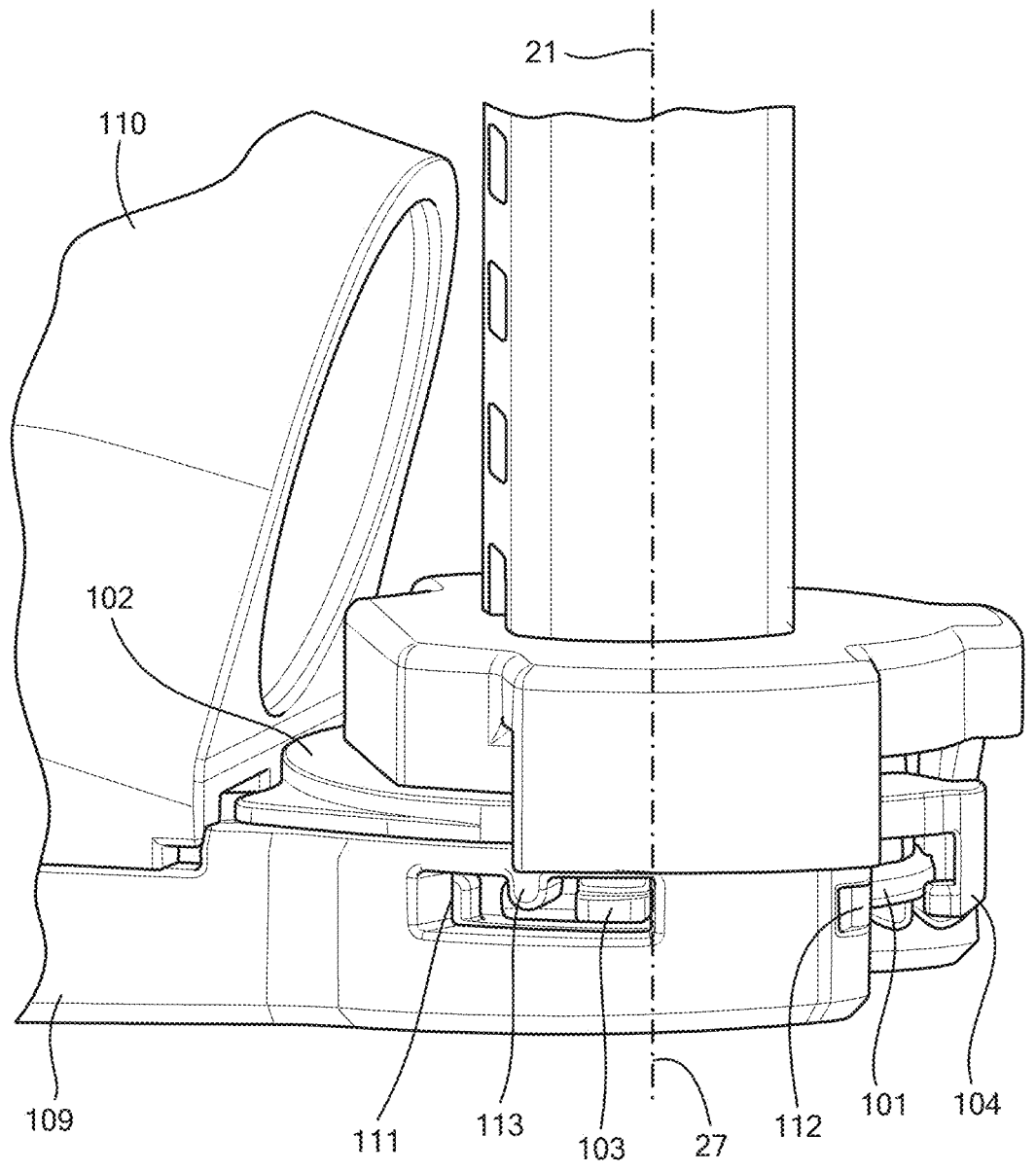
FIG. 18A depicts a side view of the needle cover and needle as it engages with the delivery housing before being rotated into a secured configuration in accordance with illustrative embodiments of the invention.

FIG. 18A schematically shows a side view of the needle loading system 100 in the delivery housing 109 in the unsecured position. To load a needle 101 and suture 107 into the delivery housing 109 for delivery into a patient 12, the medical professional 14 lowers the needle loading system 100 onto the delivery housing 109. The delivery housing 109 is connected to an endoscope cuff 110 that is fitted on the distal end of an endoscope 18. The delivery housing 109 may also be directly coupled with an endoscope 18. After the needle loading system 100 is in the delivery housing 109, the medical professional 14 then rotates the loading tool 105, which rotates the needle cover 102 and needle 101 within the delivery housing 109. By rotating the needle cover 102, the side tabs 103 slide within the side slots, past the side slot protrusion 113 and secure into the delivery housing. The front tabs 104 slide into the front slots 112, further securing the needle cover 102 on the delivery housing 109. The loading tool 105 is then removed from the needle cover 102 and needle 101 by pulling up on the loading tool 105, transitioning the needle loading system 100 into the delivery configuration for deployment into a patient 12. Upon completion of the medical procedure, or if the needle 101 and suture 107 need to be replaced, the medical professional 14 recouples the loading tool 105 onto the needle cover 102 and needle 101. The medical professional 14 then rotates the loading tool 105, rotating the needle cover 102 and needle 101, unlocking the needle cover 102 from the delivery housing 109. After the needle cover 102 is unsecured from the delivery housing 109, the medical professional 14 may pull up on the needle loading system 100, removing it from the delivery housing 109 for easy disposal or replacement.

Figure 18B:
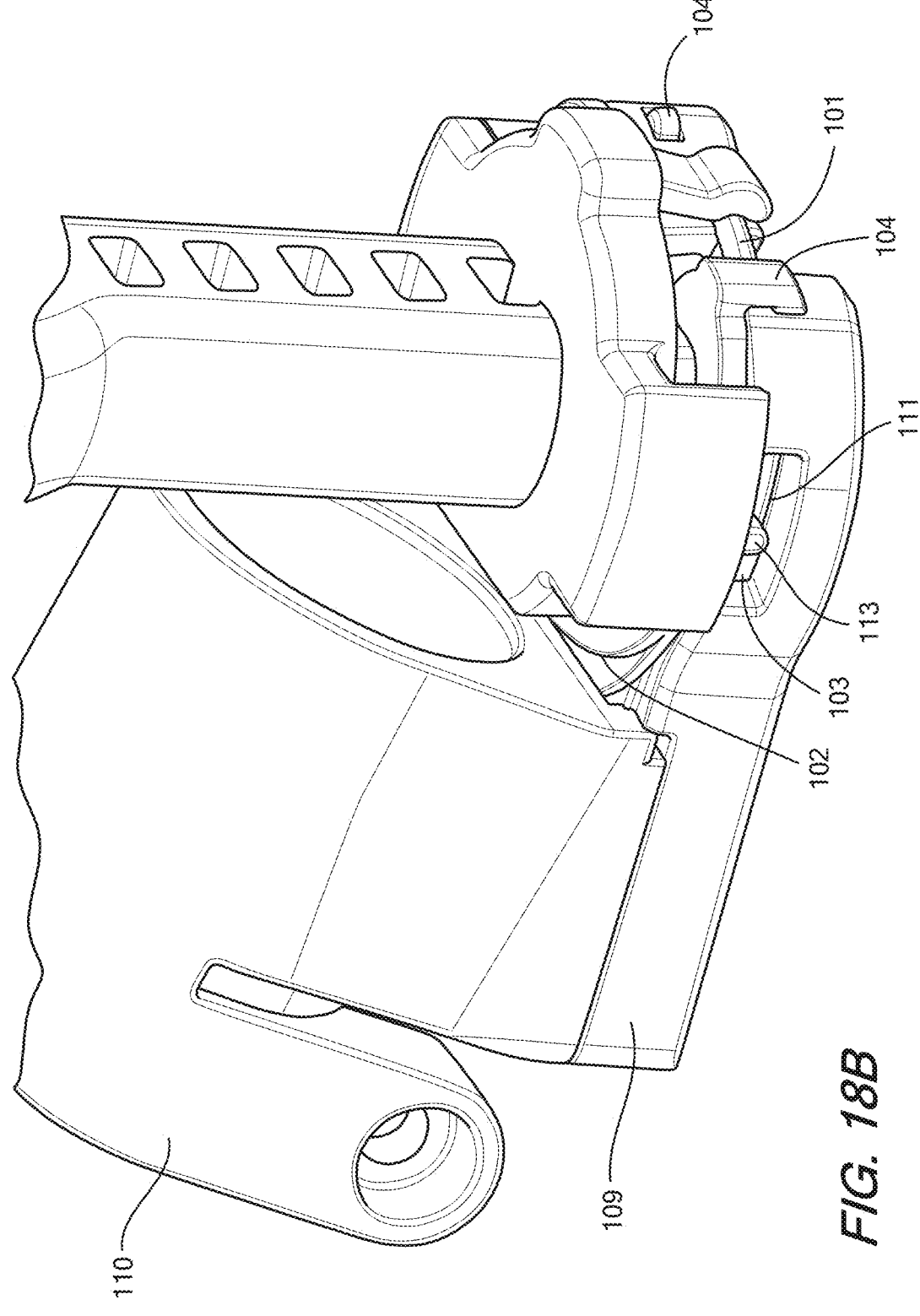
FIG. 18B depicts the needle loading system of FIG. 18A with the needle cover in a secured configuration with the delivery housing.

FIG. 18B schematically shows the needle loading system 100 in the secured configuration. Having aligned with the delivery housing 109 and rotated into a secured position, the needle cover 102 couples to the delivery housing 109 and the needle 101 is housed in the needle track 133. The front tabs 104 have rotated and secured within the front slots 112. The side tabs 103 have rotated past the delivery housing 109 slot protrusion 113 and secured within the side slots 111. In this configuration, the needle 101 and suture 107 are able to be deployed into the patient 12 and may move freely within the needle track 133 to perform the suturing procedure.

Figure 19:
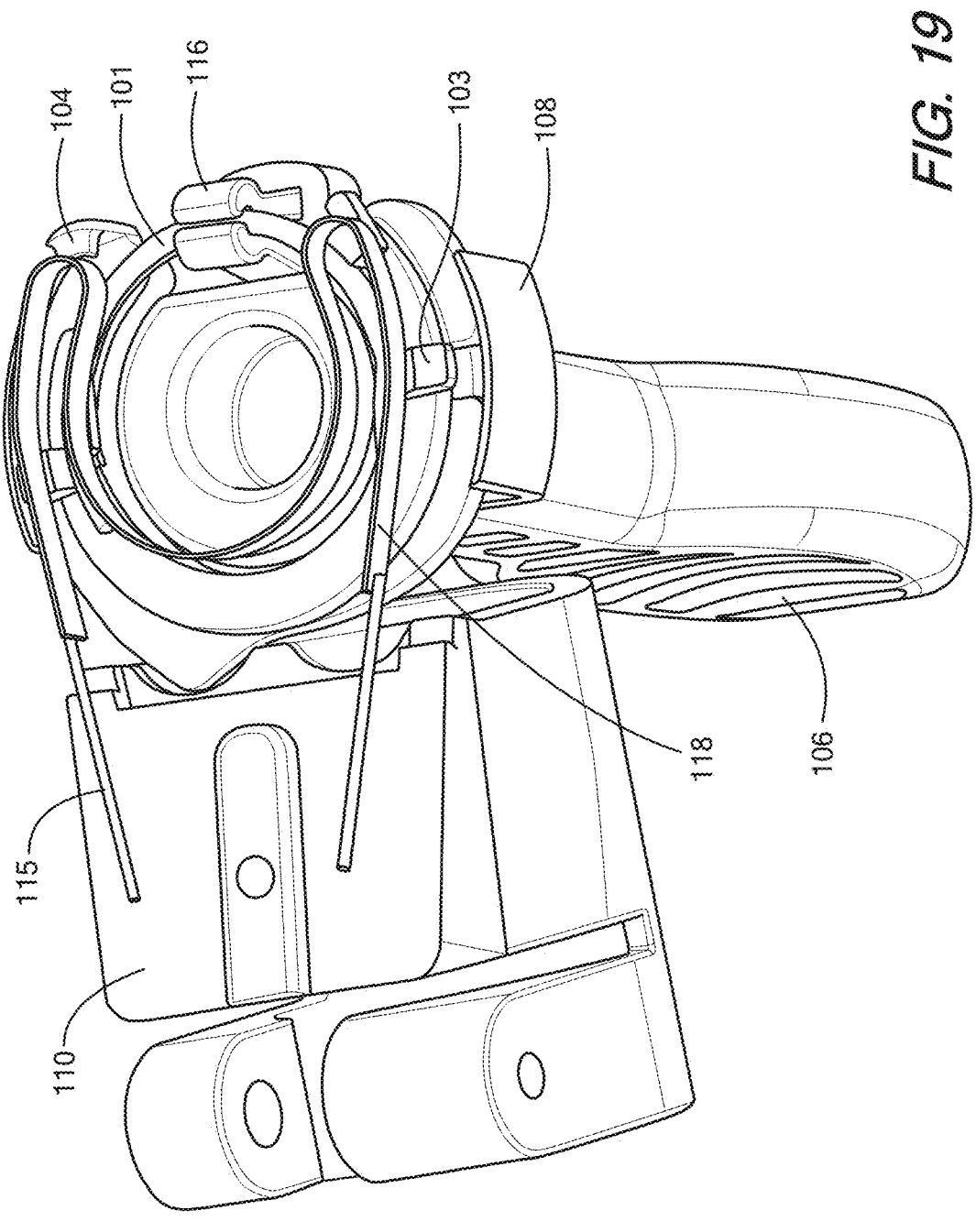
FIG. 19 depicts a bottom view of the needle loading system as it is engaged with the delivery housing and endoscope cap in accordance with illustrative embodiments of the invention.

FIG. 19 schematically shows a bottom view of the needle loading system 100 as secured into the delivery housing 109 (the delivery housing 109 is omitted in this view for clarity). The needle 101 engages a drive belt 118 that controls the needle 101 during the medical procedure. The needle 101 may engage the drive belt 118 using a corresponding notch 119 (e.g., in the needle 101) and a pawl 114 (e.g., on the drive belt 118). Operating (e.g., pulling by a medical professional) the control wires 115 (also referred to as pull wires 115) drives the drive belt 118 to rotate the needle 101 back and forth for suturing. The operation of the drive belt 118 to suture is described in more detail in U.S. patent application Ser. No. 16/433,710, which is incorporated by reference, in its entirety, herein.

The pull wires 115 may be situated outside of the endoscope 18, or within the working channel 38 of the endoscope 18, or within the endoscope of 18 (e.g., the suturing mechanism is part of the endoscope 18). As shown in FIG. 19, the needle loading system 100 is in the coupled configuration and secured into the delivery housing 109 (the delivery housing 109, again, is omitted for clarity). The loading tool 105 is coupled to the needle cover 102 by arms 108 and to the needle 101 by a needle coupling portion 116. To transition to the delivery configuration, the medical professional 14 pulls the loading tool 105, decoupling it from the needle cover 102 and needle 101. After the loading tool 105 is removed from the needle cover 102 and needle 101, the system is in the delivery configuration and may be deployed into a patient 12.

Figure 20:
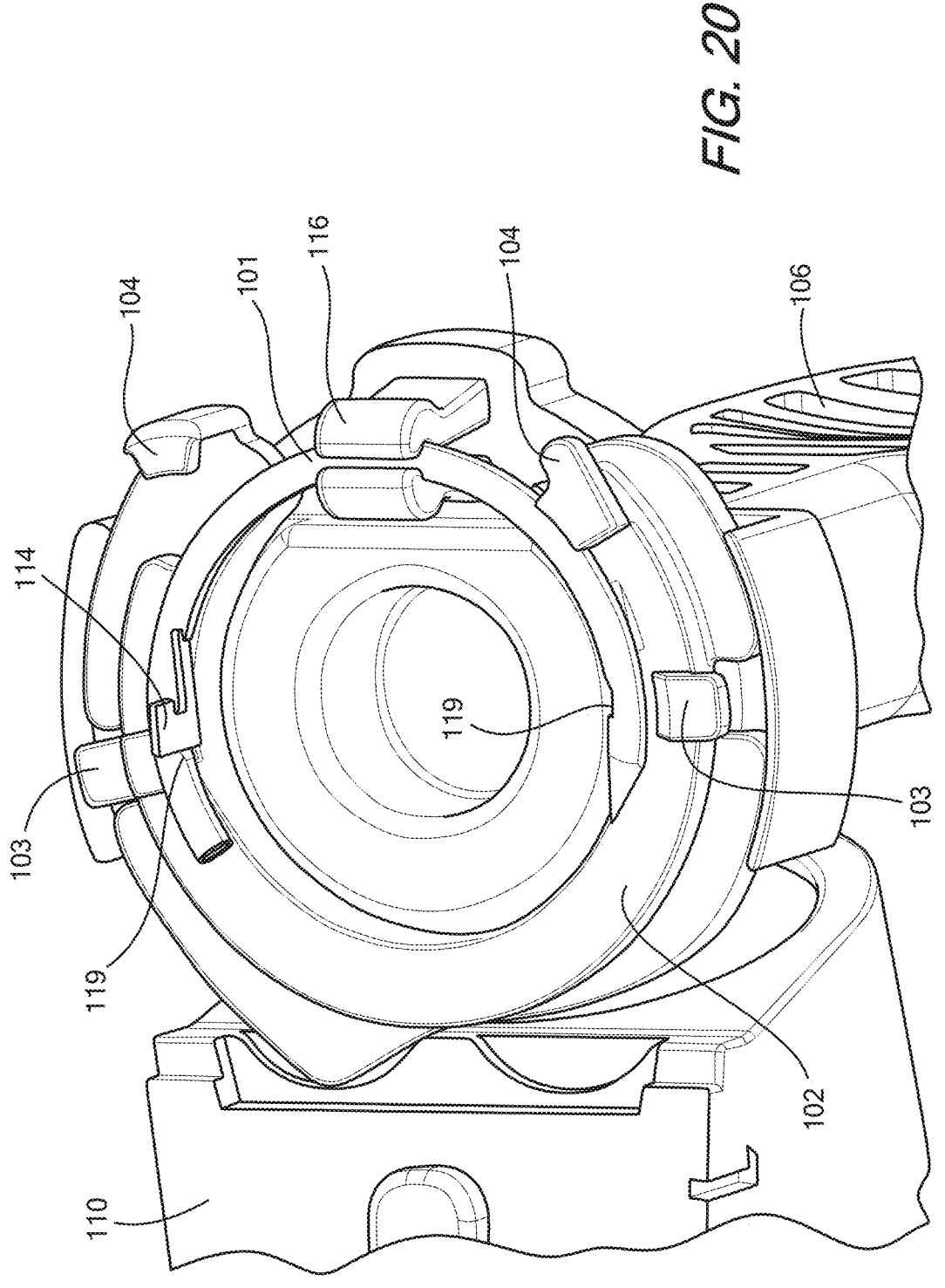
FIG. 20 depicts a bottom view of the needle loading system as it is engaged with the delivery housing and endoscope cap. The delivery housing is transparent to illustrate details of the needle placement in the delivery housing in accordance with illustrative embodiments of the invention.

FIG. 20 schematically shows a bottom view of the needle loading system 100 as secured into the delivery housing 109 (not shown) in the coupled configuration. After the needle cover 102 is secured into the delivery housing 109, the medical professional 14 may remove the loading tool 105 by pulling it from the needle cover 102. After in the delivery configuration, the needle 101 engages with a pawl 114 that controls the needle 101 during the medical procedure. The needle 101 has notches 119 that catch the pawl 114 which in turn rotates the needle 101 to suture a patient 12. The pawl 114 is coupled with the drive belt 118 (not shown), which is in turn coupled with pull wires 115. The medical professional 14 pulls on one of the pull wires 115 to move the drive belt 118 and the pawl 114. The pawl 114 catches on a needle notch 119, rotating the needle 101 in a first direction for suturing. The medical professional 14 then pulls on the other pull wire 115, moving the belt 118 and the pawl 114 in the opposite direction, catching on the other needle notch 119, moving the needle 101 in the opposite direction for suturing. By alternating the direction of the needle 101 rotation, the medical professional 14 is able to suture a patient 12 during a medical procedure. Upon completion of the medical procedure, or if the needle 101 and suture 107 need to be replaced, the medical professional 14 recouples the loading tool 105 onto the needle cover 102 and needle 101. The medical professional then rotates the loading tool 105, rotating the needle cover 102 and needle 101, unlocking the needle cover 102 from the delivery housing 109. After the needle cover 102 is unsecured from the delivery housing 109, the medical professional 14 may pull up on the needle loading system 100, removing it from the delivery housing 109 for easy disposal or replacement.

Figure 21:
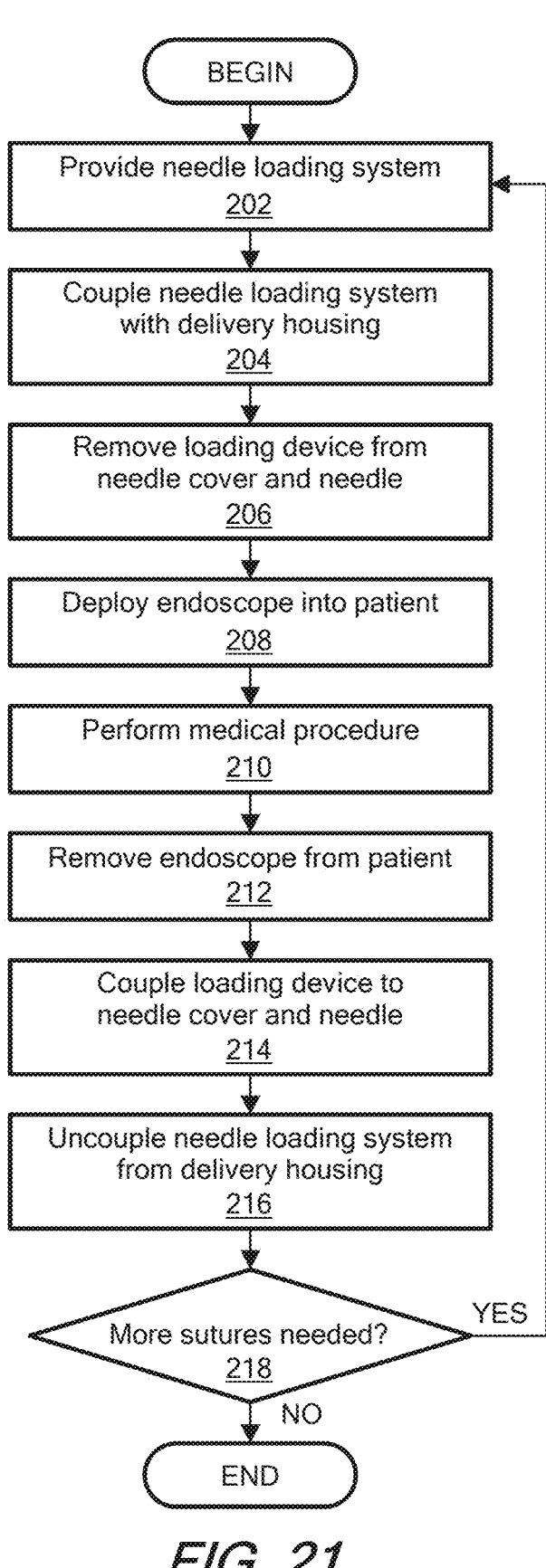
FIG. 21 depicts a method of utilizing the needle loading system to load an arcuate needle onto an endoscope, perform a medical procedure, and remove the needle from the endoscope.

FIG. 21 shows a process of suturing using the loading tool 105 in accordance with illustrative embodiments of the invention. It should be noted that this method is substantially simplified from a longer process that may normally be used. Accordingly, the method shown in FIG. 21 may have many other steps that those skilled in the art likely would use. In addition, some of the steps may be performed in a different order than that shown, or at the same time. Furthermore, some of these steps may be optional in some embodiments. Accordingly, the process 200 is merely exemplary of one process in accordance with illustrative embodiments of the invention. Those skilled in the art therefore can modify the process as appropriate.

The process begins at step 202, which provides a needle loading system 100 as described in various embodiments. The needle loading system 100 may include the loading tool 105 coupled with the needle cover 102, which may also be coupled with the needle 101, as described previously. Preferably, the needle 101 is pre-coupled with the suture 107. The needle 101, suture 107, needle cover 102, and loading tool 105 may come as a single packaged kit.

The process then proceeds to step 204, which couples the needle loading system 100 with the suturing device. The suturing device may include the cuff 110 coupled to the distal end of the endoscope 18. The suturing device may include the delivery housing 109. In various embodiments, the needle cover 102 is coupled to the suturing device (e.g., the delivery housing 109 of the suturing device). To effect the coupling, a central longitudinal axis 21 of the loading tool 105 may align with, or be oriented substantially parallel to, the central axis 27 of the delivery housing 109. In any event, the needle 101 is at least partially aligned with a corresponding needle track 133. In some embodiments, aligning the needle cover 102 with the delivery housing 109 includes aligning the side tabs 103 with the slot 111. Additionally, or alternatively, aligning may include aligning the projections 121 with the recesses 117. Accordingly, when the needle loading system 100 couples with the delivery housing 109 (e.g., positioned onto), the needle 101 is positioned at least partially in the needle track 133 (e.g., as shown in FIG. 3B).

In some embodiments, coupling the needle loading system 100 with the suturing device includes securing the needle cover 102 to the suturing device. However, in some other embodiments, securing the needle cover 102 to the suturing device (e.g., the housing 109) may include one or more additional steps. For example, in various embodiments, the tabs 104 of the cover 102 may press downward forcefully until they engage with, and become secured in, corresponding slots 112 in the delivery housing 109 (e.g., as the needle cover 102 couples with the delivery housing 109).

In some embodiments, the cover 102 may be rotated forcefully until the tabs 104 engage with, and become secured in, corresponding slots 112 in the delivery housing 109. In some further embodiments, the tabs 103, 104 may press downward and/or rotated to engage with corresponding slots 111, 112 in the delivery housing 109. Furthermore, some embodiments may include slots 111, 112 on the needle loading system (e.g., in the needle cover 102) and corresponding tabs 103, 104 on the delivery housing 109.

Figure 22:
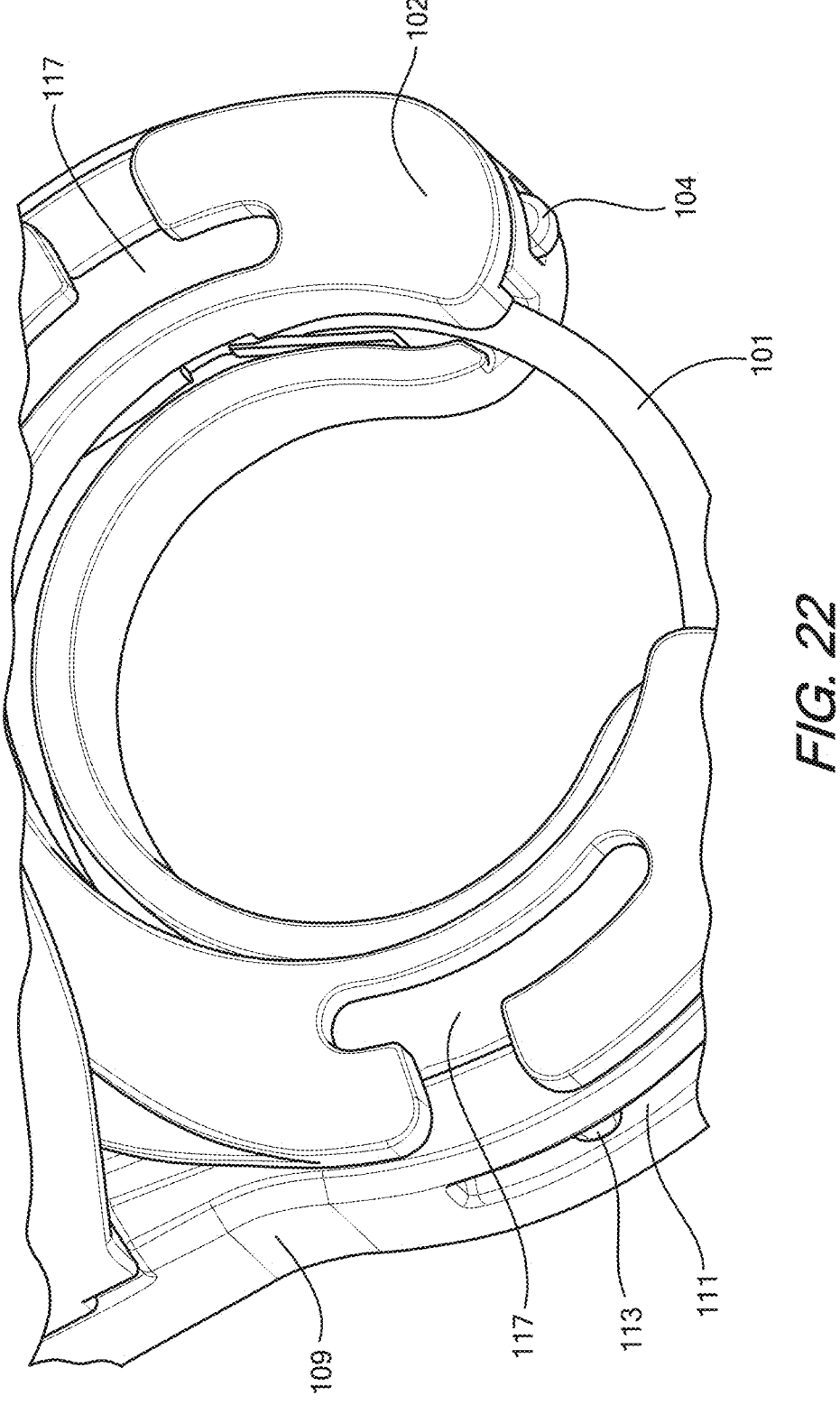
FIG. 22 depicts a top view of the needle cover in the delivery configuration with the loading tool decoupled from the needle cover and needle.
Figure 23:
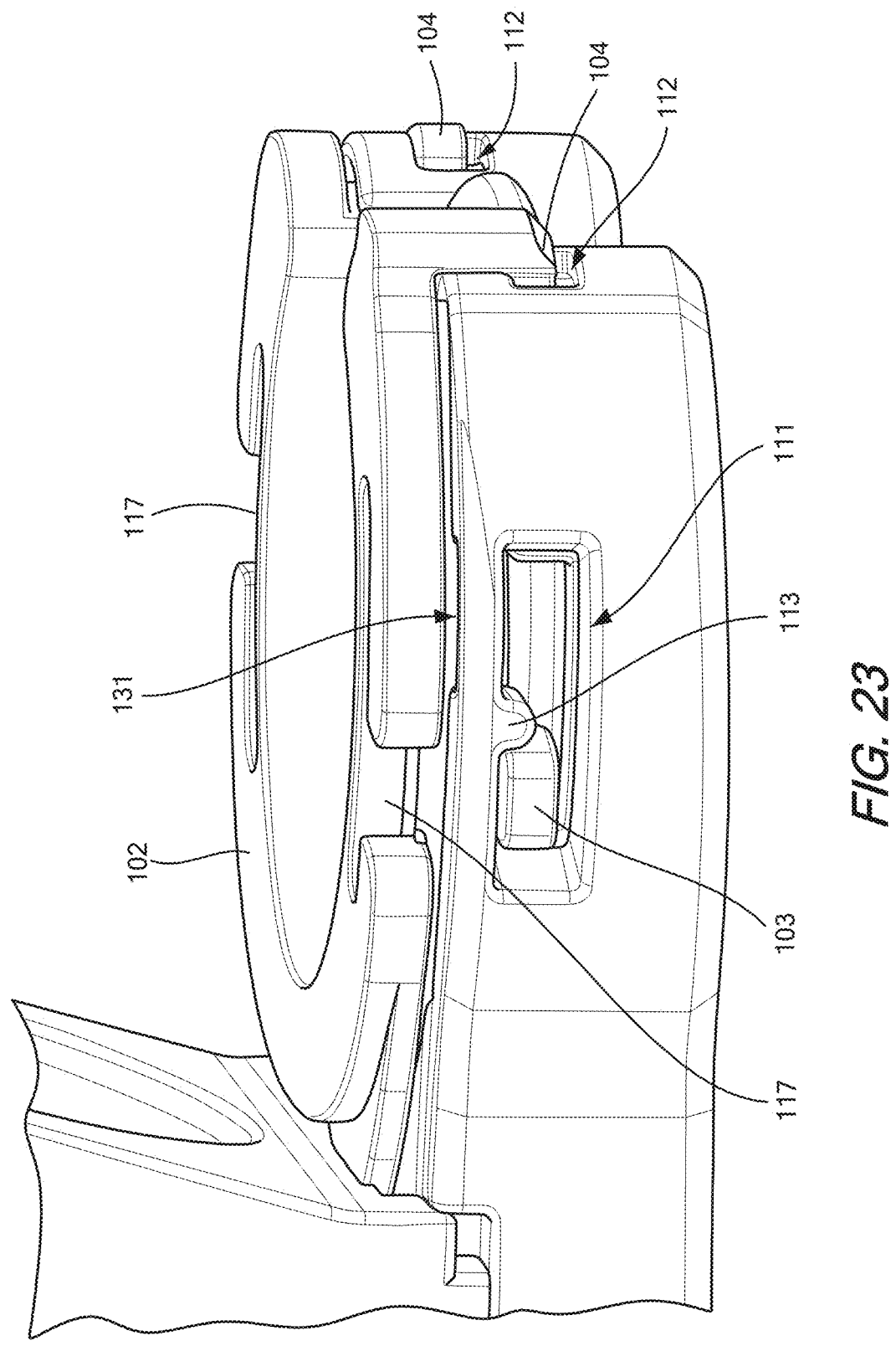
FIG. 23 depicts a side view of the needle cover with the loading tool omitted in accordance with illustrative embodiments of the invention.

FIGS. 22-23 schematically show the tabs 103 and 104 secured in the slots 111 and 112, respectively, in accordance with illustrative embodiments. In the view of FIGS. 22 and 23, the loading tool 105 is removed for clarity. However, it should be understood that at this point in the process (e.g., step 204) the loading tool 105 is still coupled with the needle cover 102. In FIG. 23, the cover 102 is securely coupled with the delivery housing 109, such that the tabs 103 are rotated beyond the protrusion 113. In various embodiments, the delivery housing 109 includes one or more openings 131 through which the tab 103 may pass to enter the slot 111. After the tab 103 rests in the slot 111, prior to removing the loading tool 105, the medical professional 14 rotates the loading tool 105 in a first direction (e.g., clockwise) to overcome a threshold force necessary for the tab 103 or the protrusion 113 to flex sufficiently for the tab 103 to settle into the position shown in FIG. 23. Alternatively, or additionally, the cover 102 is pressed downwardly as it rotates to assist with passing the protrusion 113. Thus, some embodiments may include one or more additional steps to secure the cover 102 to the housing 109 after coupling. However, some other embodiments may secure the cover 102 to the housing 109 as the two are coupled (e.g., tabs 104 may snap into slot 112 as the two components are mated).

Advantageously, the protrusion 113 in the slot 111 prevents or hinders rotation, and thereby accidentally uncoupling, of the needle cover 102 during use of the device by a medical professional. To unsecure the needle cover 102 from the housing 109, the loading tool 105 is recoupled with the needle cover 102 and rotated in a second direction opposite the first direction (e.g., counter-clockwise).

Figures 24A, 24B:
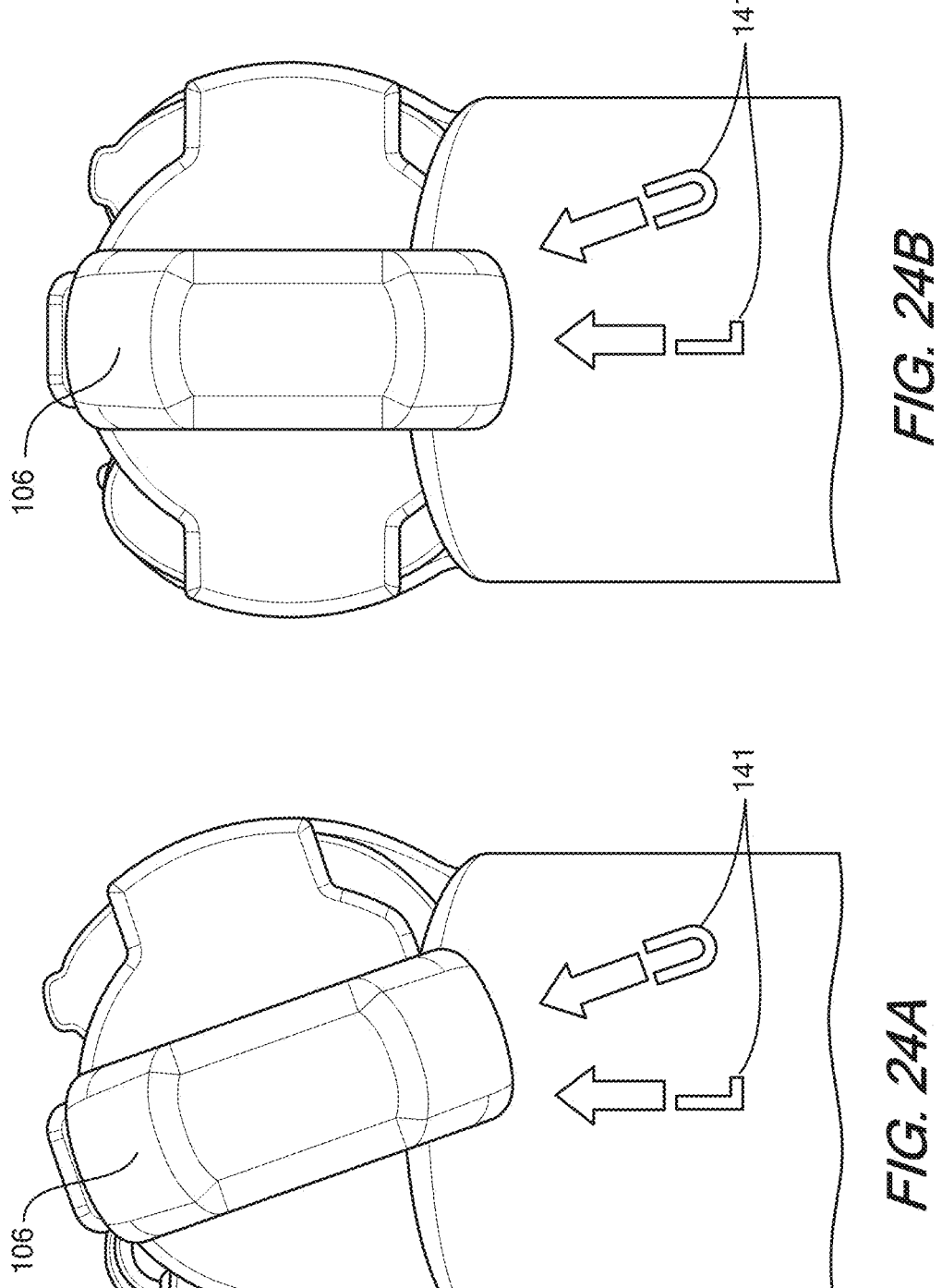
FIGS. 24A-24B depict indication markings on the suturing device in accordance with illustrative embodiments.

FIGS. 24A-24B schematically show indication markings 141 on the suturing device in accordance with illustrative embodiments. A first indication marking 141 indicates to the medical professional 14 whether the device is in the secured or unsecured configuration. In some embodiments, the indication marking 141 specifies that the loading tool 105 is rotationally in the unlocked position, as shown in FIG. 24A. A second indication marking 141 indicates that the loading tool 105 is rotationally in the locked position, as shown in FIG. 24B. In various embodiments, the indication 141 on the cuff 110 shows the current state of needle cover 102. When handle 106 aligns with L (or a locking symbol), it means the needle cover 102 is in the locked or secured position. When the handle 106 aligns with U (or an unlocking symbol), it means the needle cover 102 is in the unlocked position.

The process then proceeds to step 206, which removes the loading tool 105 from the needle cover 102 and needle 101, as shown in FIG. 16. The loading tool 105 is removed by pulling up on the loading tool when the cover is secured. This uncouples the loading tool 105 from the needle cover 102 and needle 101, transitioning the suturing system 100 into the delivery configuration.

Figures 25A, 25B:
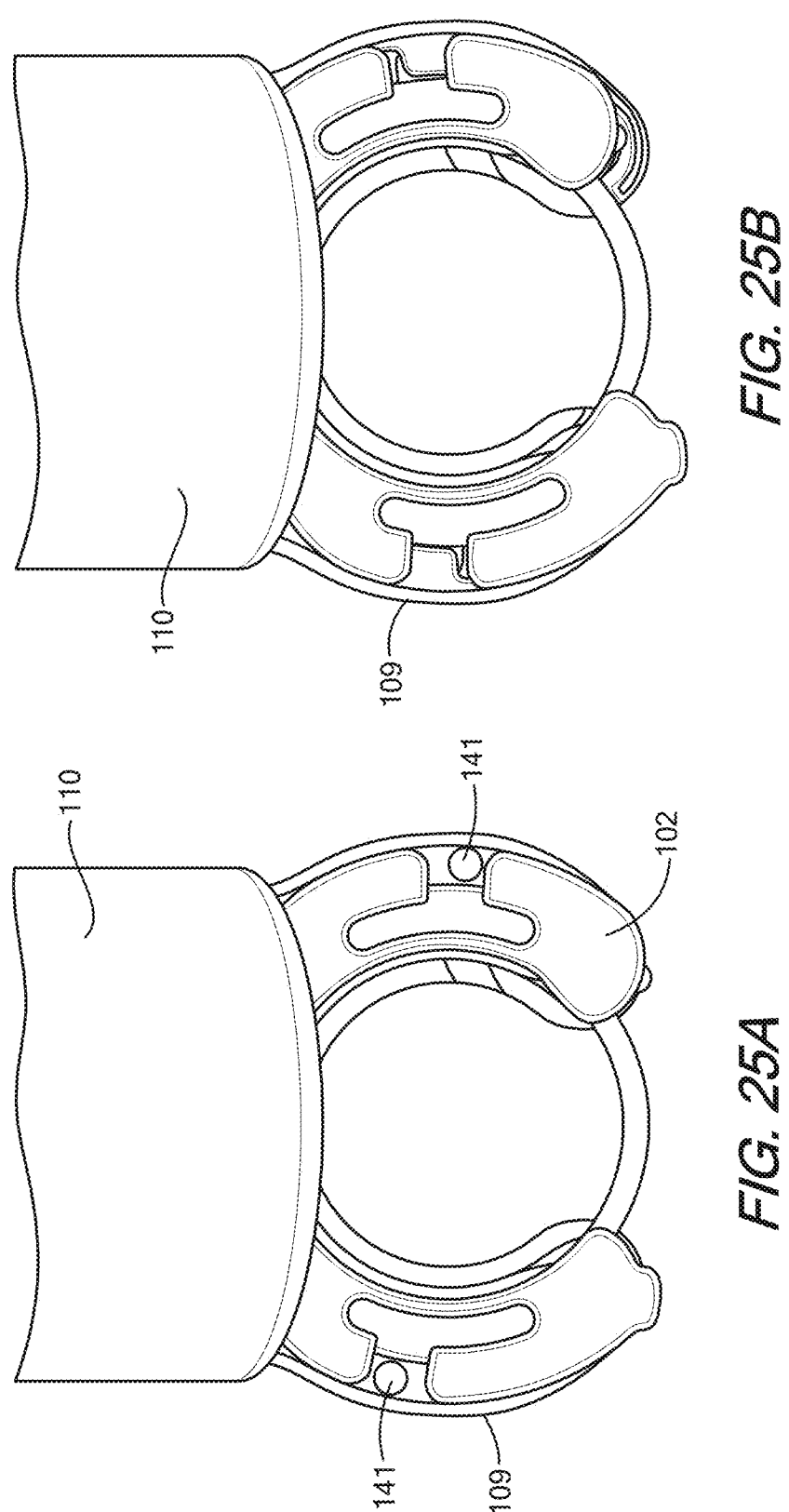
FIGS. 25A-25B depict indication markings on the housing in accordance with illustrative embodiments.

FIGS. 25A-25B schematically show an alternative embodiment of indication markings on the housing 109 in accordance with illustrative embodiments. For example, in FIG. 25A, the indicators 141 being visible indicates that the cover is secured on the delivery housing 109. In FIG. 25B, the indicators 141 being not visible indicates that the cover is unsecured on the delivery housing 109. Those skilled in the art can conceive of various ways of providing an indication for a secured or unsecured cover 102. Thus, when the tool 105 is uncoupled from the needle cover 102, the user may confirm that the needle cover 102 is in the secured or unsecured configuration.

At step 208, the endoscope 18 with the needle 101, suture 107, needle cover 102, and delivery housing 109 is deployed into the patient 12. The process proceeds to step 210 wherein the medical professional 14 performs the suturing procedure. In step 212, the endoscope 18 is removed from the patient 12 with the needle 101, needle cover 102, and delivery housing 109, while the suture 107 is left inside the patient 12. Additionally, step 212 optionally cinches any loose sutures. To that end, a suture cinching device and process may be used, as described in U.S. patent application Ser. No. 17/508,989, which is incorporated herein by reference in its entirety.

The method proceeds to step 214 where the loading tool 105 is coupled to the needle cover 102 and the needle 101 (e.g., resulting in the configuration shown in FIG. 17). The system 100 is now in the unprimed assembled configuration. To couple the loading tool 105 with the needle cover 102 and the needle 101, the arms 108 and the needle coupling portion 116 flex to surround the needle cover 102 and the needle 101, respectively. Similarly, the projections 121 may press down into the recesses 117 until they are secured therein. However, in some embodiments the loading tool 105 may only couples with the needle cover (e.g., and not the needle 101).

After the loading tool 105 and needle cover 102 are coupled, the loading system 100 may be removed from the delivery housing 109 at step 216. The medical professional 14 uncouples the needle loading system 100 from the delivery housing 109 (e.g., by pulling the system 100 upwardly after unsecuring the needle cover 102 from the housing 109). In various embodiments, the loading system 100 may be pulled up forcefully until the tabs 103, 104 disengage with corresponding slots 111, 112 in the delivery housing 109.

In some embodiments, the needle cover 104 may be rotated forcefully until the tabs 103 disengage with corresponding slots 112 in the delivery housing 109. In some further embodiments, the tool 105 may press the cover 102, and thus the tabs 103, 104, downwardly and/or rotate to disengage from the corresponding slots 111, 112. However, it should be understood by one skilled in the art that some embodiments may include slots 111, 112 on the needle loading system (e.g., in the needle cover 102) and corresponding tabs 103 on the delivery housing 109.

The process then proceeds to step 218, which asks whether more sutures are needed. If yes, the process returns to step 202 which provides a new needle loading system 100 having a new suture 107. Steps 204-218 may be repeated again. If no more sutures are needed at step 218, the process comes to an end.

As used in this specification and the claims, the singular forms "a," "an," and "the" refer to plural referents unless the context clearly dictates otherwise. For example, reference to "a suture" in the singular includes a plurality of sutures, and reference to "the needle" in the singular includes one or more needles and equivalents known to those skilled in the art. Thus, in various embodiments, any reference to the singular includes a plurality, and any reference to more than one component can include the singular. For example, reference to a plurality of arms 108 is also intended to include use of a single arm 108.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein.

It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Various inventive concepts may be embodied as one or more methods, of which examples have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Although the above discussion discloses various exemplary embodiments of the invention, it should be apparent that those skilled in the art can make various modifications that will achieve some of the advantages of the invention without departing from the true scope of the invention.

What is claimed is:

1. A system for loading an endoscopic needle into an endoscopic suturing device, the system comprising:
   a loading tool having a handle portion configured to be manipulated and a needle cover coupling portion configured to removably couple with a needle cover; and
   the needle cover configured to couple with a delivery housing, wherein the delivery housing includes one or more slots configured to receive one or more tabs of the needle cover, the needle cover configured to secure a needle within a needle track of the delivery housing when secured with the delivery housing,
   the system being configured so that the loading tool secures the needle cover to the delivery housing, the system further configured so that the loading tool unsecures the needle cover from the delivery housing.

2. The system of claim 1, wherein the loading tool comprises a needle coupling portion.

3. The system of claim 2, further comprising a needle in the needle coupling portion.

4. The system of claim 3, further comprising a suture coupled with an end of the needle.

5. The system of claim 1, further comprising an endoscopic suturing device comprising the delivery housing.

6. The system of claim 5, further comprising a drive mechanism configured to control movement of the needle.

7. The system of claim 6, wherein the drive mechanism includes a cable and a pawl.

8. The system of claim 1, wherein the one or more slots include a protrusion configured to interfere with the one or more tabs of the needle cover.

9. The system of claim 1, wherein the delivery housing includes an opening to receive the one or more tabs into the one or more slots.

10. The system of claim 1, wherein the needle cover is configured to secure to the delivery housing by pressing down the loading tool and/or rotating the loading tool in a first direction.

11. The system of claim 10, wherein the needle cover is configured to unsecure from the delivery housing by pulling up the rotating tool and/or rotating the loading tool in a second direction opposite the first direction.

12. A method of loading an endoscopic needle into an endoscopic suturing device, the method comprising:

providing a loading system including:

a loading tool having a handle portion configured to be manipulated by a medical professional, a needle cover coupling portion configured to removably couple with a needle cover, the needle cover configured to couple with a delivery housing of an endoscopic suturing system, the needle cover configured to secure a needle within a needle track of the delivery housing when coupled with the delivery housing, and a needle coupled to the loading tool and/or the needle cover;

positioning the needle within the needle track of the delivery housing of the endoscopic suturing system;

securing the needle cover to the delivery housing by using the loading tool, wherein securing the needle cover to the delivery housing comprises rotating the loading tool in a first direction;

uncoupling the loading tool from the needle cover and/or the needle, wherein uncoupling comprises pulling up on the loading tool with respect to the needle cover and/or the needle;

coupling the loading tool with the needle cover and/or the needle, wherein coupling comprises pressing down the loading tool onto the needle cover and/or the needle; and unsecuring the needle cover from the delivery housing by rotating the loading tool.

13. The method of claim 12, wherein coupling the loading tool with the needle provides a tactile feel to the medical professional.

14. The method of claim 12, further comprising:

coupling the needle with a drive mechanism; and using the drive mechanism to control the needle to suture a patient.

15. The method of claim 12, wherein unsecuring the needle cover from the delivery housing by rotating the loading tool comprises rotating the loading tool in a second direction opposite the first direction.

16. A system for loading an endoscopic needle into an endoscopic suturing device, the system comprising:

a loading tool having a handle portion configured to be manipulated by a medical professional and a needle cover coupling portion configured to removably couple with a needle cover; and the needle cover configured to couple with a delivery housing, the needle cover configured to secure a needle within a needle track of the delivery housing when secured with the delivery housing, the system being configured so that the loading tool secures the needle cover to the delivery housing, the system further configured so that the loading tool unsecures the needle cover from the delivery housing, wherein the needle cover is configured to secure to the delivery housing by pressing down the loading tool and/or rotating the loading tool in a first direction, wherein the needle cover is configured to unsecure from the delivery housing by pulling up the loading tool and/or rotating the loading tool in a second direction opposite the first direction.

17. The system of claim 16, wherein the loading tool comprises a needle coupling portion.

18. The system of claim 17, further comprising a needle in the needle coupling portion.

19. The system of claim 18, further comprising a suture coupled with an end of the needle.

20. The system of claim 16, further comprising a drive mechanism configured to control movement of the needle.

21. The system of claim 20, wherein the drive mechanism includes a cable and a pawl.

* * * * *